(12) United States Patent
Sharma et al.

(10) Patent No.: US 11,670,298 B2
(45) Date of Patent: Jun. 6, 2023

(54) SYSTEM AND METHOD FOR DATA AUGMENTATION FOR MULTI-MICROPHONE SIGNAL PROCESSING

(71) Applicant: Nuance Communications, Inc., Burlington, MA (US)

(72) Inventors: Dushyant Sharma, Woburn, MA (US); Patrick A. Naylor, Reading (GB); Rong Gong, Vienna (AT); Stanislav Kruchinin, Vienna (AT); Ljubomir Milanovic, Vienna (AT)

(73) Assignee: Nuance Communications, Inc., Burlington, MA (US)

( * ) Notice: Subject to any disclaimer, the term of this patent is extended or adjusted under 35 U.S.C. 154(b) by 0 days.

(21) Appl. No.: 17/314,718

(22) Filed: May 7, 2021

(65) Prior Publication Data
US 2021/0352406 A1 Nov. 11, 2021

Related U.S. Application Data

(60) Provisional application No. 63/022,269, filed on May 8, 2020.

(51) Int. Cl.
*G10L 15/22* (2006.01)
*G06N 20/00* (2019.01)
(Continued)

(52) U.S. Cl.
CPC .............. *G10L 15/22* (2013.01); *G06F 16/65* (2019.01); *G06F 16/686* (2019.01); *G06N 20/00* (2019.01); *G10L 15/20* (2013.01); *G10L 15/32* (2013.01); *G10L 17/06* (2013.01); *G10L 21/028* (2013.01); *G10L 25/78* (2013.01); *G10L 25/84* (2013.01); *G16H 15/00* (2018.01); *H04R 1/406* (2013.01);
(Continued)

(58) Field of Classification Search
CPC ......... G10L 15/22; G10L 25/84; G06N 20/00; H04R 1/406; H04R 29/005; H04R 3/005
USPC .................... 381/58, 56, 57, 300, 73.1, 94.1
See application file for complete search history.

(56) References Cited

U.S. PATENT DOCUMENTS 5,930,749 A 7/1999 Maes
6,009,396 A 12/1999 Nagata
(Continued)

FOREIGN PATENT DOCUMENTS

WO 2017220816 A1 12/2017

OTHER PUBLICATIONS

Non-Final Office Action issued in related U.S. Appl. No. 17/315,857 dated Jul. 9, 2021.
(Continued)

*Primary Examiner* — Thjuan K Addy
(74) *Attorney, Agent, or Firm* — Brian J. Colandreo; Heath M. Sargeant; Holland & Knight LLP

(57) ABSTRACT

A method, computer program product, and computing system for receiving a signal from each microphone of a plurality of microphones, thus defining a plurality of signals. Harmonic distortion associated with at least one microphone may be determined. One or more harmonic distortion-based augmentations may be performed on the plurality of signals based upon, at least in part, the harmonic distortion associated with the at least one microphone, thus defining one or more harmonic distortion-based augmented signals.

20 Claims, 13 Drawing Sheets

(51) Int. Cl.

| | | |
|---|---|---|
| *G10L 25/84* | (2013.01) | |
| *H04R 1/40* | (2006.01) | |
| *H04R 29/00* | (2006.01) | |
| *H04R 3/00* | (2006.01) | |
| *G10L 15/32* | (2013.01) | |
| *G10L 15/20* | (2006.01) | |
| *G06F 16/65* | (2019.01) | |
| *G06F 16/68* | (2019.01) | |
| *G10L 17/06* | (2013.01) | |
| *G10L 25/78* | (2013.01) | |
| *H04R 3/04* | (2006.01) | |
| *H04R 5/04* | (2006.01) | |
| *H04S 7/00* | (2006.01) | |
| *G16H 15/00* | (2018.01) | |
| *G10L 21/028* | (2013.01) | |
| *G10L 15/26* | (2006.01) | |
| *G16H 10/60* | (2018.01) | |
| *G16H 40/20* | (2018.01) | |
| *G10L 21/0216* | (2013.01) | |
| *G10L 21/0272* | (2013.01) | |

(52) U.S. Cl.
CPC .............. *H04R 3/005* (2013.01); *H04R 3/04* (2013.01); *H04R 5/04* (2013.01); *H04R 29/005* (2013.01); *H04S 7/307* (2013.01); *G10L 15/26* (2013.01); *G10L 21/0216* (2013.01); *G10L 21/0272* (2013.01); *G10L 2021/02166* (2013.01); *G16H 10/60* (2018.01); *G16H 40/20* (2018.01)

(56) References Cited

U.S. PATENT DOCUMENTS

| | | |
|---|---|---|
| 6,084,973 A | 7/2000 | Green et al. |
| 6,130,949 A | 10/2000 | Aoki |
| 6,178,248 B1 | 1/2001 | Marash |
| 6,600,824 B1 | 7/2003 | Matsuo |
| 6,748,086 B1 | 6/2004 | Venkatesh |
| 8,666,090 B1 | 3/2014 | Townsend |
| 8,885,815 B1 | 11/2014 | Velusamy |
| 8,949,120 B1 | 2/2015 | Every et al. |
| 9,197,974 B1 | 11/2015 | Clark et al. |
| 9,202,456 B2 | 12/2015 | Lee et al. |
| 9,305,530 B1 | 4/2016 | Durham et al. |
| 9,412,354 B1 | 8/2016 | Ramprashad |
| 9,472,188 B1 | 10/2016 | Ouimette |
| 9,508,357 B1 | 11/2016 | Krishnaswamy |
| 9,516,409 B1 | 12/2016 | Ramprashad et al. |
| 9,532,138 B1 | 12/2016 | Allen |
| 9,749,747 B1 | 8/2017 | Kriegel et al. |
| 9,820,036 B1 | 11/2017 | Tritschler et al. |
| 9,858,340 B1 | 1/2018 | Frey et al. |
| 9,866,308 B1 | 1/2018 | Bultan |
| 9,892,744 B1 | 2/2018 | Salonidis |
| 9,900,685 B2 | 2/2018 | Varerkar et al. |
| 9,900,694 B1 | 2/2018 | List |
| 9,900,723 B1 | 2/2018 | Choisel |
| 9,972,339 B1 | 5/2018 | Sundaram |
| 10,037,756 B2 | 7/2018 | Pellom |
| 10,090,000 B1 | 10/2018 | Tzirkel-Hancock |
| 10,313,786 B1 | 6/2019 | Bao et al. |
| 10,381,022 B1 | 8/2019 | Chaudhuri |
| 10,424,315 B1 | 9/2019 | Ganeshkumar |
| 10,431,238 B1 | 10/2019 | Biruski et al. |
| 10,540,883 B1 | 1/2020 | Keil |
| 10,566,012 B1 | 2/2020 | Basye et al. |
| 10,622,004 B1 | 4/2020 | Zhang |
| 10,643,609 B1 | 5/2020 | Pogue et al. |
| 10,777,214 B1 | 9/2020 | Shi |
| 10,887,709 B1 | 1/2021 | Mansour et al. |
| 10,924,872 B2 | 2/2021 | Gunawan et al. |
| 11,039,013 B1 | 6/2021 | Garrod |
| 11,158,335 B1 | 10/2021 | Ganguly |
| 11,551,670 B1 | 1/2023 | Smith et al. |
| 2002/0048376 A1 | 4/2002 | Ukita |
| 2002/0095290 A1 | 7/2002 | Kahn et al. |
| 2002/0097885 A1 | 7/2002 | Birchfield |
| 2003/0027600 A1 | 2/2003 | Krasny |
| 2003/0033148 A1 | 2/2003 | Silverman et al. |
| 2003/0051532 A1 | 3/2003 | Beaucoup |
| 2003/0228023 A1 | 12/2003 | Burnett et al. |
| 2004/0240680 A1 | 12/2004 | Rui |
| 2005/0265562 A1 | 12/2005 | Rui |
| 2006/0239471 A1 | 10/2006 | Mao et al. |
| 2006/0250998 A1 | 11/2006 | Beaucoup et al. |
| 2006/0262943 A1 | 11/2006 | Oxford |
| 2007/0041586 A1 | 2/2007 | Stone et al. |
| 2007/0053524 A1 | 3/2007 | Haulick et al. |
| 2008/0091421 A1 | 4/2008 | Gustavsson |
| 2008/0167869 A1 | 7/2008 | Nakadai |
| 2008/0170715 A1 | 7/2008 | Zhang |
| 2008/0177536 A1 | 7/2008 | Sherwani |
| 2009/0022332 A1 | 1/2009 | Van Schaack |
| 2009/0055178 A1 | 2/2009 | Coon |
| 2009/0089053 A1 | 4/2009 | Wang |
| 2009/0175466 A1 | 7/2009 | Elko et al. |
| 2009/0198495 A1 | 8/2009 | Hata |
| 2009/0202089 A1* | 8/2009 | Zhang ................... H04R 1/222 381/174 |
| 2009/0214048 A1* | 8/2009 | Stokes, III ............... H04B 3/23 381/66 |
| 2009/0259466 A1 | 10/2009 | Stubley et al. |
| 2010/0142327 A1 | 6/2010 | Kepesi |
| 2010/0188929 A1 | 7/2010 | Kitaura |
| 2010/0211387 A1 | 8/2010 | Chen |
| 2010/0241426 A1 | 9/2010 | Zhang |
| 2010/0296668 A1 | 11/2010 | Lee |
| 2011/0075859 A1 | 3/2011 | Kim |
| 2011/0164761 A1 | 7/2011 | McCowan |
| 2011/0288860 A1 | 11/2011 | Schevciw |
| 2012/0123773 A1 | 5/2012 | Zeng |
| 2012/0128175 A1 | 5/2012 | Visser et al. |
| 2012/0163610 A1 | 6/2012 | Sakagami |
| 2012/0214544 A1 | 8/2012 | Shivappa et al. |
| 2012/0239394 A1 | 9/2012 | Matsumoto |
| 2013/0035777 A1 | 2/2013 | Niemisto et al. |
| 2013/0051582 A1* | 2/2013 | Kropfitsch ................ H03F 1/56 330/144 |
| 2013/0083832 A1 | 4/2013 | Sorensen |
| 2013/0322643 A1 | 5/2013 | Every et al. |
| 2013/0170666 A1 | 7/2013 | Ng et al. |
| 2013/0204618 A1 | 8/2013 | Henry et al. |
| 2013/0258813 A1 | 10/2013 | Herre |
| 2013/0282373 A1 | 10/2013 | Visser et al. |
| 2013/0304476 A1 | 11/2013 | Kim et al. |
| 2013/0332156 A1 | 12/2013 | Tackin et al. |
| 2014/0098972 A1 | 4/2014 | Yamada |
| 2014/0105416 A1 | 4/2014 | Huttunen et al. |
| 2014/0143582 A1 | 5/2014 | Kindred |
| 2014/0149117 A1 | 5/2014 | Bakish et al. |
| 2014/0270231 A1 | 9/2014 | Dusan et al. |
| 2014/0286497 A1 | 9/2014 | Thyssen et al. |
| 2014/0321664 A1 | 10/2014 | Huang et al. |
| 2014/0334645 A1 | 11/2014 | Yun et al. |
| 2014/0348342 A1 | 11/2014 | Laaksonen et al. |
| 2015/0063579 A1 | 3/2015 | Bao |
| 2015/0185312 A1 | 7/2015 | Gaubitch |
| 2015/0228274 A1 | 8/2015 | Leppanen |
| 2015/0302869 A1 | 10/2015 | Tomlin et al. |
| 2015/0340048 A1 | 11/2015 | Shioda et al. |
| 2015/0341722 A1 | 11/2015 | Iyengar |
| 2016/0014490 A1 | 1/2016 | Bar Bracha et al. |
| 2016/0044411 A1 | 2/2016 | Tawada |
| 2016/0050488 A1 | 2/2016 | Matheja et al. |
| 2016/0073203 A1 | 3/2016 | Kuriger |
| 2016/0035370 A1 | 4/2016 | Krini et al. |
| 2016/0125882 A1 | 5/2016 | Contolini et al. |
| 2016/0180743 A1 | 6/2016 | Ahmad |
| 2016/0189728 A1 | 6/2016 | Chen |
| 2016/0261951 A1 | 9/2016 | Matheja et al. |
| 2016/0322055 A1 | 11/2016 | Sainath et al. |

(56) References Cited

U.S. PATENT DOCUMENTS

| | | |
|---|---|---|
| 2017/0047079 A1 | 2/2017 | Hiroe |
| 2017/0257709 A1 | 9/2017 | Cohen et al. |
| 2017/0287470 A1 | 10/2017 | Pellom et al. |
| 2017/0307721 A1 | 10/2017 | Sugiyama et al. |
| 2018/0018970 A1 | 1/2018 | Heyl et al. |
| 2018/0176679 A1 | 6/2018 | Lu et al. |
| 2018/0197559 A1 | 7/2018 | Orescanin et al. |
| 2018/0262832 A1 | 9/2018 | Grosche et al. |
| 2018/0270565 A1 | 9/2018 | Ganeshkumar |
| 2018/0294000 A1 | 10/2018 | Steele et al. |
| 2018/0309496 A1 | 10/2018 | Lee |
| 2018/0322888 A1 | 11/2018 | Tsukagoshi |
| 2018/0374495 A1 | 12/2018 | Fienberg et al. |
| 2019/0046126 A1 | 2/2019 | Owen et al. |
| 2019/0051375 A1 | 2/2019 | Owen et al. |
| 2019/0058847 A1 | 2/2019 | Mayer et al. |
| 2019/0082269 A1* | 3/2019 | Sun .................... H04R 19/04 |
| 2019/0082271 A1* | 3/2019 | Kim .................... H04R 19/005 |
| 2019/0189144 A1 | 6/2019 | Dusan |
| 2019/0208318 A1 | 7/2019 | Chowdhary |
| 2019/0272905 A1 | 9/2019 | Almendro |
| 2019/0318743 A1 | 10/2019 | Reshef et al. |
| 2019/0318757 A1 | 10/2019 | Chen et al. |
| 2019/0341050 A1 | 11/2019 | Diamant et al. |
| 2019/0341058 A1 | 11/2019 | Zhang |
| 2019/0373362 A1 | 12/2019 | Ansai et al. |
| 2019/0373390 A1 | 12/2019 | Horbach |
| 2019/0385635 A1 | 12/2019 | Tov et al. |
| 2020/0034113 A1 | 1/2020 | Holst et al. |
| 2020/0066295 A1 | 2/2020 | Karimian-azar et al. |
| 2020/0096580 A1 | 3/2020 | Hoecht |
| 2020/0098346 A1 | 3/2020 | Kemmerer |
| 2020/0126565 A1 | 4/2020 | Kim et al. |
| 2020/0184985 A1 | 6/2020 | Nesta et al. |
| 2020/0213726 A1 | 7/2020 | Dyrholm |
| 2020/0312315 A1 | 10/2020 | Li et al. |
| 2020/0335088 A1 | 10/2020 | Gao et al. |
| 2020/0349928 A1 | 11/2020 | Mandal et al. |
| 2020/0349950 A1 | 11/2020 | Yoshioka et al. |
| 2020/0374624 A1 | 11/2020 | Koschak |
| 2020/0394887 A1 | 12/2020 | Heath |
| 2020/0395003 A1 | 12/2020 | Sharma et al. |
| 2020/0395109 A1 | 12/2020 | Owen |
| 2020/0410045 A1 | 12/2020 | Vozilla et al. |
| 2021/0021927 A1 | 1/2021 | Harmke et al. |
| 2021/0035563 A1 | 2/2021 | Cartwright et al. |
| 2021/0065686 A1 | 3/2021 | Rao |
| 2021/0074282 A1 | 3/2021 | Borgstrom et al. |
| 2021/0098098 A1 | 4/2021 | Pinto |
| 2021/0116519 A1 | 4/2021 | Weiss |
| 2021/0118435 A1 | 4/2021 | Stahl |
| 2021/0134280 A1 | 5/2021 | Kurtz |
| 2021/0161498 A1 | 6/2021 | Hu |
| 2021/0174811 A1 | 6/2021 | Ebenezer et al. |
| 2021/0193131 A1 | 6/2021 | Hook |
| 2021/0210200 A1 | 7/2021 | Gallopyn |
| 2021/0217432 A1 | 7/2021 | Zheng |
| 2021/0233652 A1 | 7/2021 | Owen |
| 2021/0241782 A1 | 8/2021 | Ganeshkumar |
| 2021/0243412 A1 | 8/2021 | Owen |
| 2021/0329390 A1 | 10/2021 | Rottier |
| 2021/0337307 A1 | 10/2021 | Wexler et al. |
| 2021/0350804 A1 | 11/2021 | Sharma et al. |
| 2021/0350808 A1 | 11/2021 | Sharma et al. |
| 2021/0350809 A1 | 11/2021 | Sharma et al. |
| 2021/0350813 A1 | 11/2021 | Sharma et al. |
| 2021/0350814 A1 | 11/2021 | Sharma |
| 2021/0350815 A1 | 11/2021 | Sharma |
| 2021/0350822 A1 | 11/2021 | Liu et al. |
| 2021/0352404 A1 | 11/2021 | Sharma et al. |
| 2021/0352405 A1 | 11/2021 | Sharma et al. |
| 2021/0352406 A1 | 11/2021 | Sharma |
| 2022/0059114 A1 | 2/2022 | Emanuel et al. |
| 2022/0180882 A1 | 6/2022 | Wang et al. |
| 2022/0248135 A1 | 8/2022 | Chen et al. |
| 2022/0270625 A1 | 8/2022 | Dai et al. |
| 2022/0286788 A1 | 9/2022 | Carlile et al. |
| 2023/0058427 A1 | 2/2023 | Pakarinen et al. |

OTHER PUBLICATIONS

Cornelis, B., Moonen, M. and Wouters, J., "Binaural voice activity detection for MWF-based noise reduction in binaural hearing aids,", 2011, 2011 19th European Signal Processing Conference, pp. 486-490 (Year: 2011).

Non-Final Office Action issued in related U.S. Appl. No. 17/315,892 dated Jul. 14, 2021.

Non-Final Office Action issued in related U.S. Appl. No. 17/315,829 dated Jul. 16, 2021.

Non-Final Office Action issued in related U.S. Appl. No. 17/315,955 dated Jul. 28, 2021.

Yoshioka et al. "Meeting Transcription Using Asynchronous Distant Microphones," INTERSPEECH 2019. Retrieved on Jul. 7, 2021.

Dvorkind et al., "Time difference of Arrival Estimation of Speech Source in a Noisy and Reverberant Environment," CCIT Report #457, Dec. 2003, Retrieved on Apr. 4, 2021.

International Search Report and Written Opinion issued in PCT/US2021/031516 dated Aug. 9, 2021.

International Search Report and Written Opinion issued in PCT/US2021/031508 dated Aug. 6, 2021.

International Search Report and Written Opinion issued in PCT/US2021/031363 dated Aug. 26, 2021.

International Search Report and Written Opinion issued in PCT/US2021/031369 dated Aug. 26, 2021.

International Search Report and Written Opinion issued in PCI/US2021/031374 dated Aug. 16, 2021.

International Search Report and Written Opinion issued in PCT/US2021/031378 dated Sep. 8, 2021.

International Search Report and Written Opinion issued in PCT/US2021/031498 dated Aug. 10, 2021.

International Search Report and Written Opinion issued in PCT/US2021/031504 dated Aug. 6, 2021.

International Search Report and Written Opinion issued in PCT/US2021/031512 dated Aug. 16, 2021.

Thomas et al., "Analyzing Convolutional Neural Networks for Speech Activity Detection in Mismatched Acoustic Conditions," IEEE International Conference on Acoustic, Speech and Signal Processing (2014).

Final Office Action issued in counterpart U.S. Appl. No. 17/315,829 dated Oct. 25, 2021.

Final Office Action issued in counterpart U.S. Appl. No. 17/315,829 dated Nov. 16, 2021.

Final Office Action issued in counterpart U.S. Appl. No. 17/315,916 dated Nov. 5, 2021.

Final Office Action issued in U.S. Appl. No. 17/315,857 dated Dec. 1, 2021.

Notice of Allowance issued in U.S. Appl. No. 17/315,857 dated Nov. 4, 2021.

Notice of Allowance issued in U.S. Appl. No. 17/315,916 dated Jan. 25, 2022.

Non-Final Office Action issued in U.S. Appl. No. 17/315,890 dated Feb. 16, 2022.

Non-Final Office Action Issued in U.S. Appl. No. 17/315,955 dated Mar. 29, 2022.

Non-Final Office Action issued in U.S. Appl. No. 17/315,955 dated Apr. 27, 2022.

Final Office Action issued in U.S. Appl. No. 17/315,890 dated May 31, 2022.

Non-Final Office Action issued in U.S. Appl. No. 17/315,829 dated Jun. 3, 2022.

Non-Final Office Action issued in U.S. Appl. No. 17/314,660 dated Jun. 30, 2022.

"Final Office Action issued in U.S. Appl. No. 17/315,955", dated Aug. 30, 2022, 14 Pages.

"Notice of Allowance Issued in U.S. Appl. No. 17/314,527", dated Sep. 30, 2022, 7 Pages.

(56) References Cited

OTHER PUBLICATIONS

"Notice of Allowance Issued in U.S. Appl. No. 17/314,660", dated Nov. 14, 2022, 7 Pages.
"Notice of Allowance Issued in U.S. Appl. No. 17/315,857", dated Oct. 27, 2021, 40 Pages.
"Notice of Allowance Issued in U.S. Appl. No. 17/315,890", dated Sep. 8, 2022, 9 Pages.
"Notice of Allowance Issued In U.S. Appl. No. 17/314,527", dated Jan. 12, 2023, 8 Pages.
"Notice of Allowance Issued in U.S. Appl. No. 17/315,890", dated Jan. 13, 2023, 8 Pages.
"Notice of Allowance Issued in U.S. Appl. No. 17/314,660", dated Feb. 9, 2023, 7 Pages.
"Non Final Office Action Issued In U.S. Appl. No. 17/314,601" dated Mar. 29, 2023, 15 Pages.
U.S Appl. No. 17/314,660, filed May 7, 2021.
U.S Appl. No. 17/314,601, filed May 7, 2021.
U.S Appl. No. 17/315,857, filed May 10, 2021.
U.S Appl. No. 17/314,527, filed May 7, 2021.
U.S Appl. No. 17/315,955, filed May 10, 2021.
U.S Appl. No. 17/315,890, filed May 10, 2021.
U.S Appl. No. 17/315,916, filed May 10, 2021.
U.S Appl. No. 17/315,829, filed May 10, 2021.

* cited by examiner

SYSTEM AND METHOD FOR DATA AUGMENTATION FOR MULTI-MICROPHONE SIGNAL PROCESSING

RELATED APPLICATION(S)

This application claims the benefit of the following U.S. Provisional Application No. 63/022,269 filed on 8 May 2020, the contents of which are all incorporated herein by reference.

BACKGROUND

Automated Clinical Documentation (ACD) may be used, e.g., to turn transcribed conversational (e.g., physician, patient, and/or other participants such as patient's family members, nurses, physician assistants, etc.) speech into formatted (e.g., medical) reports. Such reports may be reviewed, e.g., to assure accuracy of the reports by the physician, scribe, etc.

To improve the accuracy of speech processing of ACD, data augmentation may allow for the generation of new training data for a machine learning system by augmenting existing data to represent new conditions. For example, data augmentation has been used to improve robustness to noise and reverberation, and other unpredictable characteristics of speech in a real world deployment (e.g., issues and unpredictable characteristics when capturing speech signals in a real world environment versus a controlled environment).

Various physical characteristics of audio recording systems may result in degradation of speech processing performance. For example, microelectro-mechanical system (MEMS) microphones may generally include mechanical devices that sense the acoustic air pressure and form the main sensor for acoustic signal acquisition in most popular consumer devices (e.g., mobile phones, video conferencing systems and multi-microphone array systems).

MEMS microphones may suffer from various imperfections. For example, known imperfections in these MEMS microphones generally include microphone sensitivity imperfections, microphone self-noise, microphone frequency response, and harmonic distortions.

When designing multi-microphone systems or arrays, it is often assumed that all microphones in the system or array are perfectly well-matched. However, this is generally not accurate in real world systems. As such, while conventional approaches try to estimate these imperfections and compensate for them (e.g., typically only accounting for microphone sensitivity) or by relying on expensive calibration processes to establish the imperfections and compensate for those imperfections (which are not feasible at a large scale), the underlying enhancement algorithms rely on perfectly matched microphones.

SUMMARY OF DISCLOSURE

In one implementation, a computer-implemented method executed by a computer may include but is not limited to receiving a signal from each microphone of a plurality of microphones, thus defining a plurality of signals. Harmonic distortion associated with at least one microphone may be determined. One or more harmonic distortion-based augmentations may be performed on the plurality of signals based upon, at least in part, the harmonic distortion associated with the at least one microphone, thus defining one or more harmonic distortion-based augmented signals.

One or more of the following features may be included. Determining the total harmonic distortion associated with the at least one microphone may include receiving a harmonic distortion parameter associated with the at least one microphone. The harmonic distortion parameter may indicate an order of harmonics associated with the at least one microphone. Performing the one or more harmonic distortion-based augmentations on the plurality of signals based upon, at least in part, the harmonic distortion parameter may include generating a harmonic distortion-based augmented signal based upon, at least in part, the harmonic distortion parameter and a table of harmonic distortion coefficients. Determining the total harmonic distortion associated with the at least one microphone may include measuring the total harmonic distortion from the at least one microphone. The table of harmonic distortion coefficients may be generated based upon, at least in part, the total harmonic distortion measured from the at least one microphone. The plurality of microphones may define a microphone array.

In another implementation, a computer program product resides on a computer readable medium and has a plurality of instructions stored on it. When executed by a processor, the instructions cause the processor to perform operations including but not limited to receiving a signal from each microphone of a plurality of microphones, thus defining a plurality of signals. Harmonic distortion associated with at least one microphone may be determined. One or more harmonic distortion-based augmentations may be performed on the plurality of signals based upon, at least in part, the harmonic distortion associated with the at least one microphone, thus defining one or more harmonic distortion-based augmented signals.

One or more of the following features may be included. Determining the total harmonic distortion associated with the at least one microphone may include receiving a harmonic distortion parameter associated with the at least one microphone. The harmonic distortion parameter may indicate an order of harmonics associated with the at least one microphone. Performing the one or more harmonic distortion-based augmentations on the plurality of signals based upon, at least in part, the harmonic distortion parameter may include generating a harmonic distortion-based augmented signal based upon, at least in part, the harmonic distortion parameter and a table of harmonic distortion coefficients. Determining the total harmonic distortion associated with the at least one microphone may include measuring the total harmonic distortion from the at least one microphone. The table of harmonic distortion coefficients may be generated based upon, at least in part, the total harmonic distortion measured from the at least one microphone. The plurality of microphones may define a microphone array.

In another implementation, a computing system includes a processor and memory is configured to perform operations including but not limited to, receiving a signal from each microphone of a plurality of microphones, thus defining a plurality of signals. The processor may be further configured to determine a total harmonic distortion associated with at least one microphone. The processor may be further configured to perform one or more harmonic distortion-based augmentations on the plurality of signals based upon, at least in part, the total harmonic distortion associated with the at least one microphone, thus defining one or more harmonic distortion-based augmented signals.

One or more of the following features may be included. Determining the total harmonic distortion associated with the at least one microphone may include receiving a harmonic distortion parameter associated with the at least one microphone. The harmonic distortion parameter may indicate an order of harmonics associated with the at least one microphone. Performing the one or more harmonic distortion-based augmentations on the plurality of signals based upon, at least in part, the harmonic distortion parameter may include generating a harmonic distortion-based augmented signal based upon, at least in part, the harmonic distortion parameter and a table of harmonic distortion coefficients. Determining the total harmonic distortion associated with the at least one microphone may include measuring the total harmonic distortion from the at least one microphone. The table of harmonic distortion coefficients may be generated based upon, at least in part, the total harmonic distortion measured from the at least one microphone. The plurality of microphones may define a microphone array.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
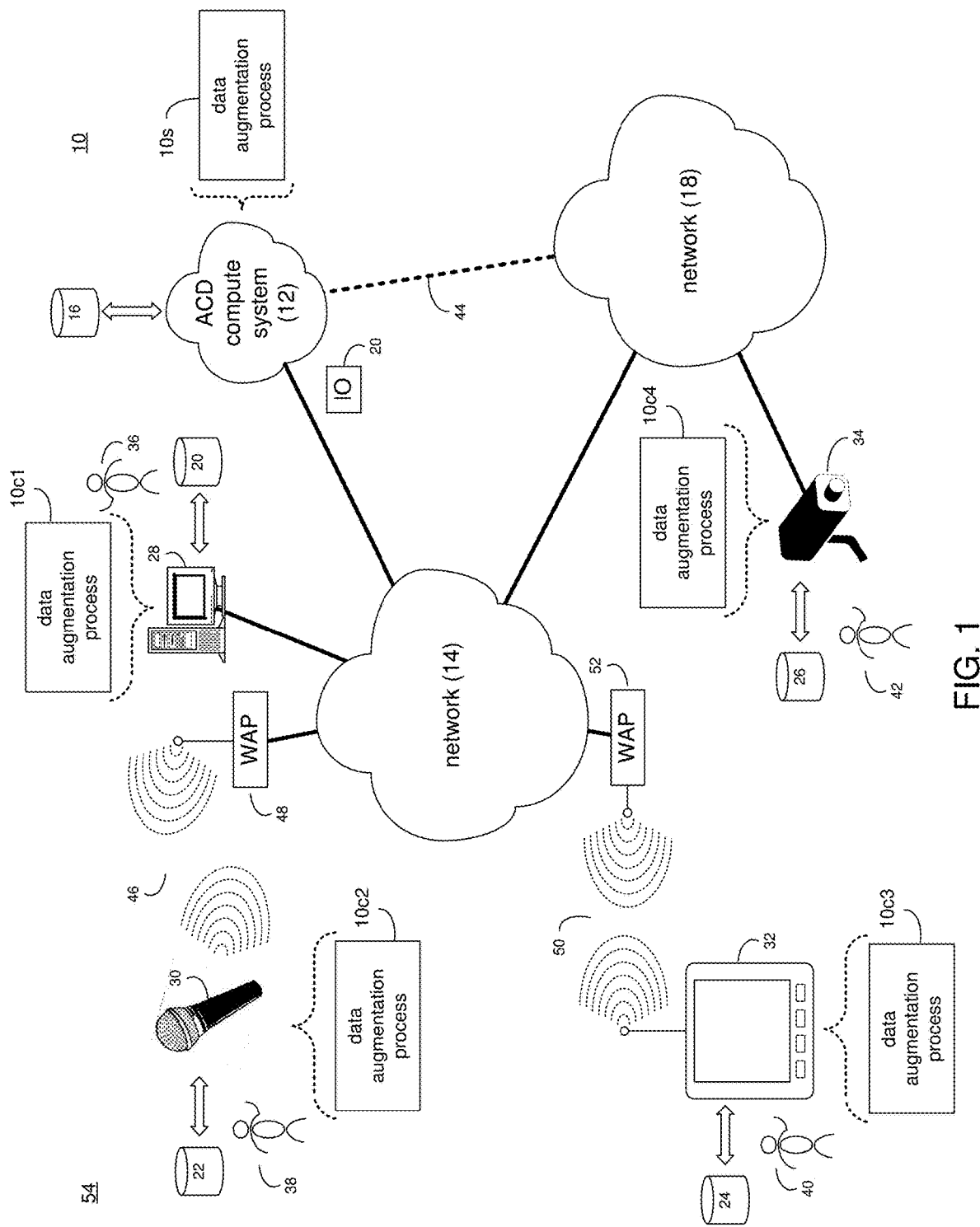
FIG. 1 is a diagrammatic view of an automated clinical documentation computer system and a data augmentation process coupled to a distributed computing network.

System Overview:

Referring to FIG. 1, there is shown data augmentation process 10. As will be discussed below in greater detail, data augmentation process 10 may be configured to automate the collection and processing of clinical encounter information to generate/store/distribute medical records.

Data augmentation process 10 may be implemented as a server-side process, a client-side process, or a hybrid server-side/client-side process. For example, data augmentation process 10 may be implemented as a purely server-side process via data augmentation process 10s. Alternatively, data augmentation process 10 may be implemented as a purely client-side process via one or more of data augmentation process 10c1, data augmentation process 10c2, data augmentation process 10c3, and data augmentation process 10c4. Alternatively still, data augmentation process 10 may be implemented as a hybrid server-side/client-side process via data augmentation process 10s in combination with one or more of data augmentation process 10c1, data augmentation process 10c2, data augmentation process 10c3, and data augmentation process 10c4.

Accordingly, data augmentation process 10 as used in this disclosure may include any combination of data augmentation process 10s, data augmentation process 10c1, data augmentation process 10c2, data augmentation process 10c3, and data augmentation process 10c4.

Data augmentation process 10s may be a server application and may reside on and may be executed by automated clinical documentation (ACD) computer system 12, which may be connected to network 14 (e.g., the Internet or a local area network). ACD computer system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACD computer system 12 may execute one or more operating systems, examples of which may include but are not limited to: Microsoft Windows Server™; Redhat Linux™, Unix, or a custom operating system, for example.

The instruction sets and subroutines of data augmentation process 10s, which may be stored on storage device 16 coupled to ACD computer system 12, may be executed by one or more processors (not shown) and one or more memory architectures (not shown) included within ACD computer system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from data augmentation process 10s, data augmentation process 10c1, data augmentation process 10c2, data augmentation process 10c3 and/or data augmentation process 10c4 to ACD computer system 12. Examples of IO request 20 may include but are not limited to data write requests (i.e. a request that content be written to ACD computer system 12) and data read requests (i.e. a request that content be read from ACD computer system 12).

The instruction sets and subroutines of data augmentation process 10c1, data augmentation process 10c2, data augmentation process 10c3 and/or data augmentation process 10c4, which may be stored on storage devices 20, 22, 24, 26

(respectively) coupled to ACD client electronic devices 28, 30, 32, 34 (respectively), may be executed by one or more processors (not shown) and one or more memory architectures (not shown) incorporated into ACD client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACD client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACD computer system 12 directly through network 14 or through secondary network 18. Further, ACD computer system 12 may be connected to network 14 through secondary network 18, as illustrated with link line 44.

The various ACD client electronic devices (e.g., ACD client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACD client electronic devices (e.g., ACD client electronic devices 28, 30, 32, 34) may each execute an operating system, examples of which may include but are not limited to Microsoft Windows™, Apple Macintosh™, Redhat Linux™, or a custom operating system, wherein the combination of the various ACD client electronic devices (e.g., ACD client electronic devices 28, 30, 32, 34) and ACD computer system 12 may form modular ACD system 54.

Figure 2:
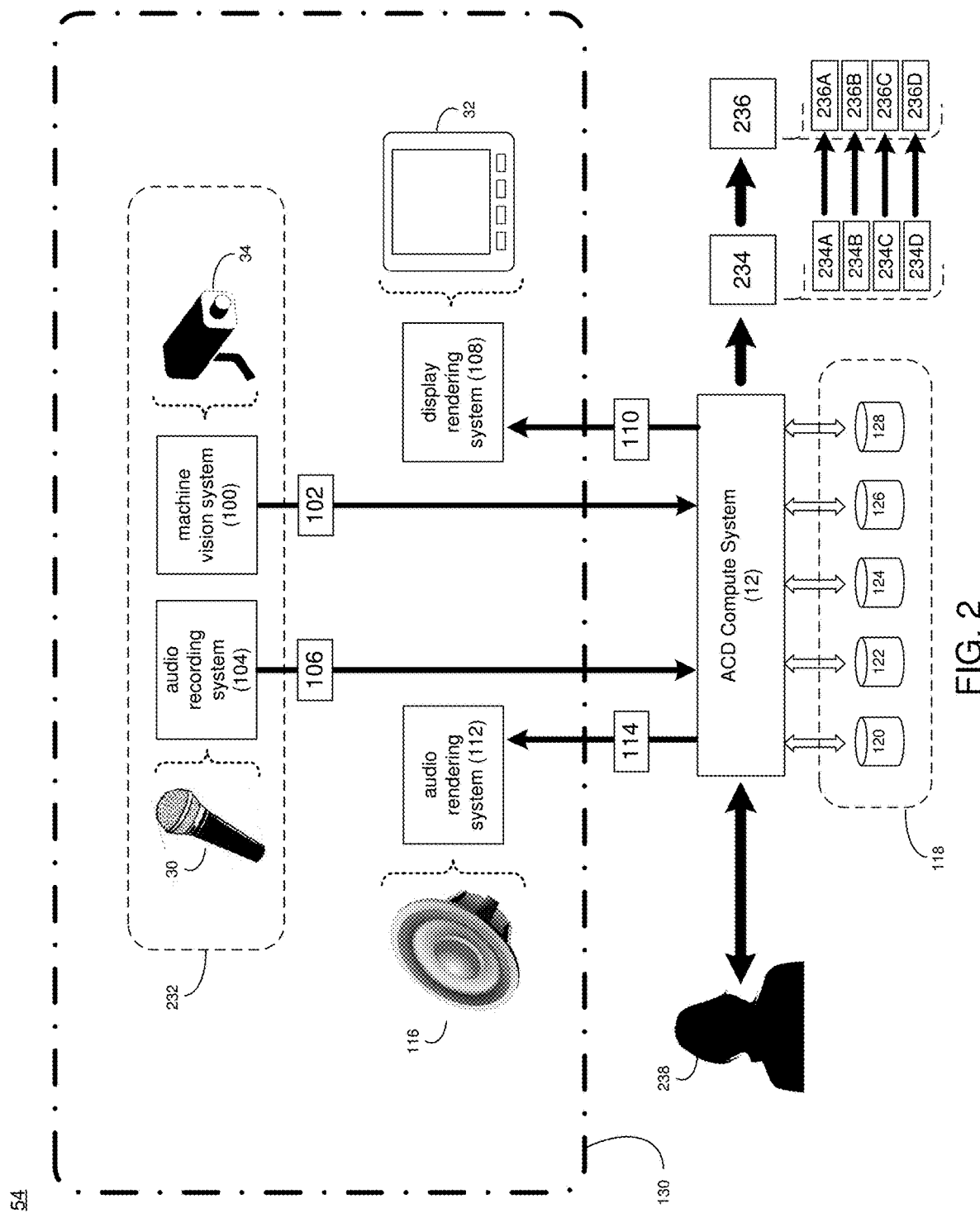
FIG. 2 is a diagrammatic view of a modular ACD system incorporating the automated clinical documentation computer system of FIG. 1.

Referring also to FIG. 2, there is shown a simplified example embodiment of modular ACD system 54 that is configured to automate clinical documentation. Modular ACD system 54 may include: machine vision system 100 configured to obtain machine vision encounter information 102 concerning a patient encounter; audio recording system 104 configured to obtain audio encounter information 106 concerning the patient encounter; and a computer system (e.g., ACD computer system 12) configured to receive machine vision encounter information 102 and audio encounter information 106 from machine vision system 100 and audio recording system 104 (respectively). Modular ACD system 54 may also include: display rendering system 108 configured to render visual information 110; and audio rendering system 112 configured to render audio information 114, wherein ACD computer system 12 may be configured to provide visual information 110 and audio information 114 to display rendering system 108 and audio rendering system 112 (respectively).

Example of machine vision system 100 may include but are not limited to: one or more ACD client electronic devices (e.g., ACD client electronic device 34, examples of which may include but are not limited to an RGB imaging system, an infrared imaging system, a ultraviolet imaging system, a laser imaging system, a SONAR imaging system, a RADAR imaging system, and a thermal imaging system). Examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Examples of display rendering system 108 may include but are not limited to: one or more ACD client electronic devices (e.g., ACD client electronic device 32, examples of which may include but are not limited to a tablet computer, a computer monitor, and a smart television). Examples of audio rendering system 112 may include but are not limited to: one or more ACD client electronic devices (e.g., audio rendering device 116, examples of which may include but are not limited to a speaker system, a headphone system, and an earbud system).

As will be discussed below in greater detail, ACD computer system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource. While in this particular example, five different examples of datasources 118, are shown, this is for illustrative purposes only and is not intended to be a limitation of this disclosure, as other configurations are possible and are considered to be within the scope of this disclosure.

As will be discussed below in greater detail, modular ACD system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACD client electronic devices (e.g., ACD client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACD client electronic devices (e.g., ACD client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACD client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACD computer system 12 may include a plurality of discrete computer systems. As discussed above, ACD computer system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACD computer system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Figure 3:
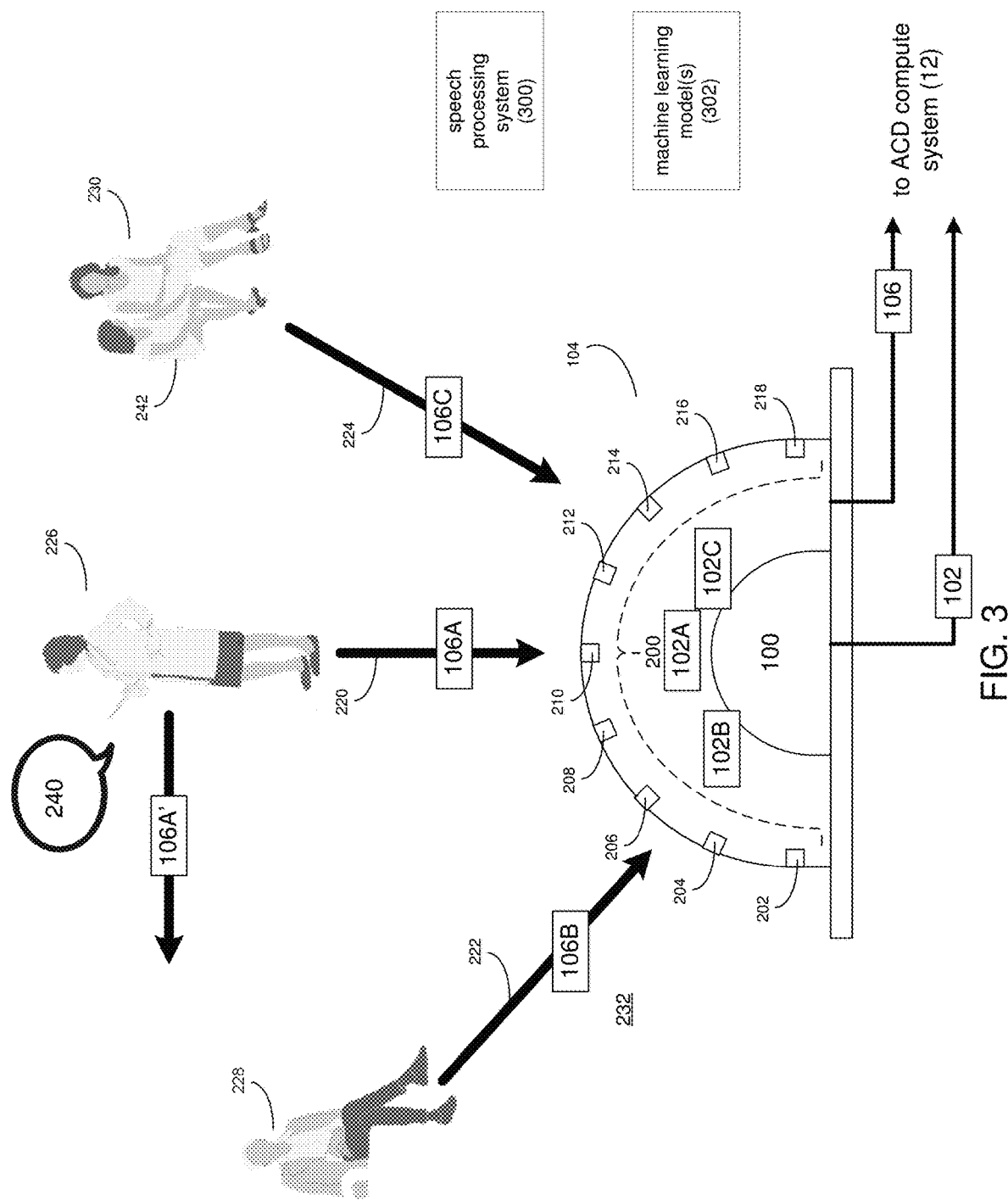
FIG. 3 is a diagrammatic view of a mixed-media ACD device included within the modular ACD system of FIG. 2.

Referring also to FIG. 3, audio recording system 104 may include directional microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACD system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, modular ACD system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACD system 54 and/or audio recording system 104 may be configured to utilize audio acquisition device 210 to form audio recording beam 220, thus enabling the capturing of audio (e.g., speech) produced by encounter participant 226 (as audio acquisition device 210 is pointed to (i.e., directed toward) encounter participant 226). Additionally, modular ACD system 54 and/or audio recording system 104 may be configured to utilize audio acquisition devices 204, 206 to form audio recording beam 222, thus enabling the capturing of audio (e.g., speech) produced by encounter participant 228 (as audio acquisition devices 204, 206 are pointed to (i.e., directed toward) encounter participant 228). Additionally, modular ACD system 54 and/or audio recording system 104 may be configured to utilize audio acquisition devices 212, 214 to form audio recording beam 224, thus enabling the capturing of audio (e.g., speech) produced by encounter participant 230 (as audio acquisition devices 212, 214 are pointed to (i.e., directed toward) encounter participant 230). Further, modular ACD system 54 and/or audio recording system 104 may be configured to utilize null-steering precoding to cancel interference between speakers and/or noise.

As is known in the art, null-steering precoding is a method of spatial signal processing by which a multiple antenna transmitter may null multiuser interference signals in wireless communications, wherein null-steering precoding may mitigate the impact off background noise and unknown user interference.

In particular, null-steering precoding may be a method of beamforming for narrowband signals that may compensate for delays of receiving signals from a specific source at different elements of an antenna array. In general and to improve performance of the antenna array, in incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACD device 232. For example, mixed-media ACD device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACD system 54 may be configured to include a plurality of mixed-media ACD devices (e.g., mixed-media ACD device 232) when the above-described clinical environment is larger or a higher level of resolution is desired.

Modular ACD system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACD device 232 (and machine vision system 100/audio recording system 104 included therein) may be configured to monitor one or more encounter participants (e.g., encounter participants 226, 228, 230) of a patient encounter.

Specifically, machine vision system 100 (either as a stand-alone system or as a component of mixed-media ACD device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACD computer system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACD system 54 (and/or mixed-media ACD device 232) is configured, ACD computer system 12 may be included within mixed-media ACD device 232 or external to mixed-media ACD device 232.

As discussed above, ACD computer system 12 may execute all or a portion of data augmentation process 10, wherein the instruction sets and subroutines of data augmentation process 10 (which may be stored on one or more of e.g., storage devices 16, 20, 22, 24, 26) may be executed by ACD computer system 12 and/or one or more of ACD client electronic devices 28, 30, 32, 34.

The Data Augmentation Process:

In some implementations consistent with the present disclosure, systems and methods may be provided for data augmentation of training data for multi-channel speech processing systems (e.g., neural enhancement (e.g., beamforming), multi-channel, end-to-end automated speech recognition (MCE2E) systems, etc.) with a range of corruption profiles that allow underlying speech processing algorithms to "learn" to become more robust to microphone system imperfections. For example and as discussed above, data augmentation allows for the generation of new training data for a machine learning system by augmenting existing data to represent new conditions. For example, data augmentation has been used to improve robustness to noise and reverberation, and other unpredictable characteristics of speech in a real world deployment (e.g., issues and unpredictable characteristics when capturing speech signals in a real world environment versus a controlled environment).

In some implementations, various physical characteristics of audio recording systems may result in degradation of speech processing performance. For example, microelectromechanical system (MEMS) microphones may generally include mechanical devices that sense the acoustic air pressure and form the main sensor for acoustic signal acquisition in most popular consumer devices (e.g., mobile phones, video conferencing systems and multi-microphone array systems). In some implementations, a microphone may generally include a discrete audio acquisition device (e.g., audio acquisition devices 202, 204, 206, 208, 210, 212, 214, 216, 218), an amplifier, and/or an analog-to-digital system.

In some implementations, MEMS microphones may suffer from various imperfections. For example, known imperfections in these MEMS microphones generally include microphone sensitivity imperfections, microphone self-noise, microphone frequency response, and harmonic distortions. As will be discussed in greater detail below, microphone sensitivity generally includes the response of the microphone to a given sound pressure level. This may vary from device to device (e.g., from microphone to microphone of a microphone array). Microphone self-noise generally includes the amount of noise output by the microphone in a perfectly quiet environment. In some implementations, the spectral shape of this noise might be such that it affects some frequencies more than others and different microphones may have a different self-noise level/characteristic. In some implementations, a microphone may have a non-flat magnitude and/or non-linear frequency response at different frequencies. In some implementations, an enclosure of the microphone or of the microphone array may introduce spectral shaping to the microphone frequency response. Harmonic distortion may be a measure of the amount of distortion on the output of a microphone for a given pure tone input signal. While several examples of microphone imperfections have been provided, it will be appreciated that other imperfections may introduce issues when performing speech processing operations using multiple microphones (e.g., as in microphone array 104) within the scope of the present disclosure.

When designing neural beamforming or MCE2E systems, it is often assumed that all microphones in the system or array are perfectly well-matched. However, for at least the reasons described above, this is generally not accurate in real world systems. As such, while conventional approaches try to estimate these imperfections and compensate for them (e.g., typically only accounting for microphone sensitivity) or by relying on expensive calibration processes to establish the imperfections and compensate for those imperfections (which are not feasible at a large scale), the underlying enhancement algorithms often rely on perfectly matched microphones.

As will be discussed in greater detail below, implementations of the present disclosure may address the imperfections between microphones by augmenting training data for beamforming and MCE2E systems with a range of corruption profiles that allow the underlying speech processing algorithms to 'learn' to become more robust to microphone system imperfections. In some implementations, the underlying speech processing system(s) may learn to address a range of microphone system or array imperfections jointly with optimization criteria for the system; instead of relying on external calibration data or auxiliary processing which itself may not be ideal as in conventional systems. Implementations of the present disclosure may also avoid any extra processing overhead to an underlying speech processing system and without requiring expensive and time-consuming microphone system calibration data. Implementations of the present disclosure may address degradations in microphone system performance over time by learning the microphone system's imperfections during training.

Figure 4:
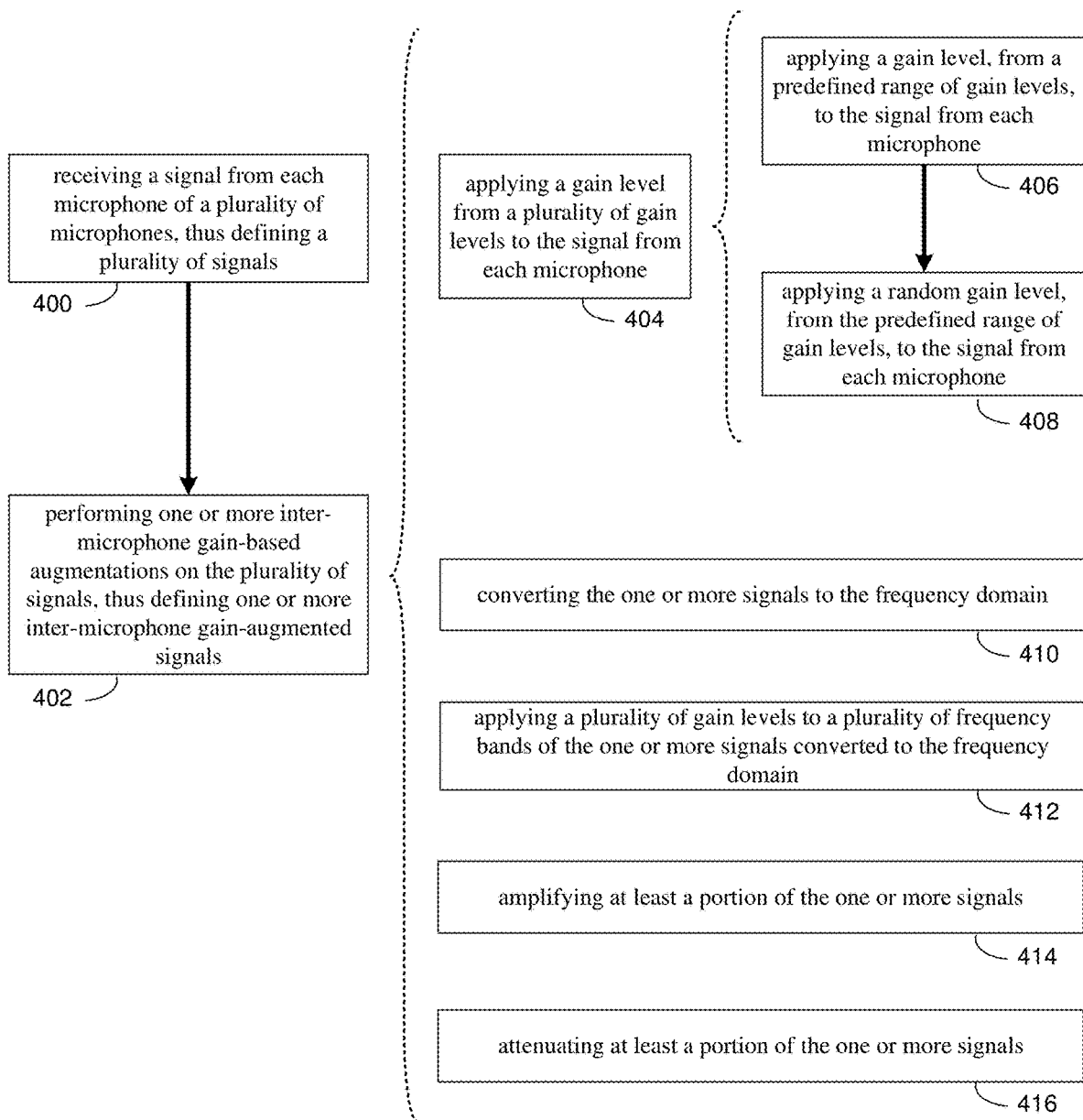
FIG. 4 is a flow chart of one implementation of the data augmentation process of FIG. 1.

As discussed above and referring also at least to FIGS. 4-6, data augmentation process 10 may receive 400 a signal from each microphone of a plurality of microphones, thus defining a plurality of signals. One or more inter-microphone gain-based augmentations may be performed 402 on the plurality of signals, thus defining one or more inter-microphone gain-augmented signals.

Figure 5:
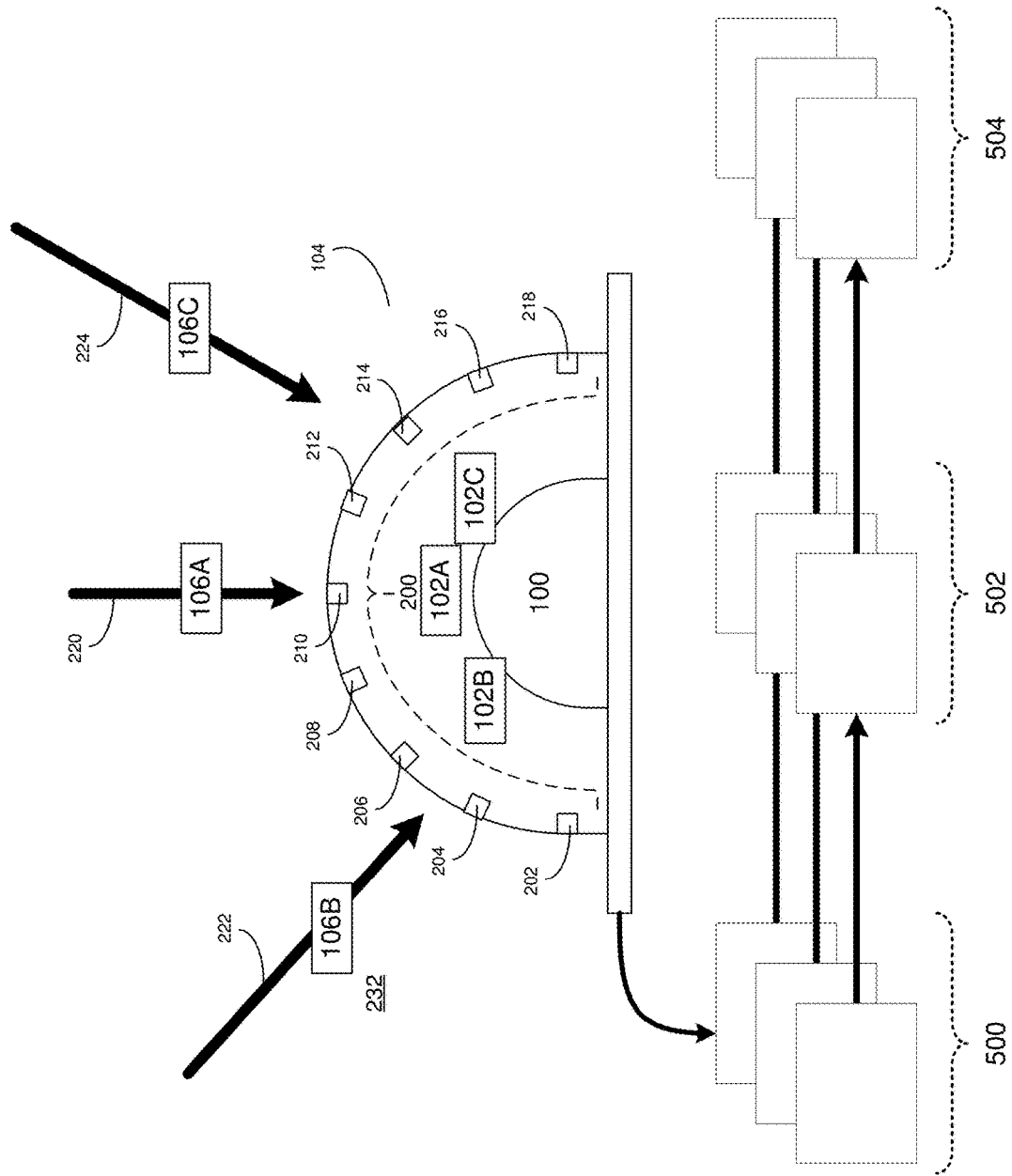
FIGS. 5-6 are diagrammatic views of a modular ACD system according to various implementations of the data augmentation process of FIG. 1.

Referring also to FIG. 5 and in some implementations, audio recording system 104 may include directional microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. In some implementations, each audio acquisition device or microphone may include a microphone assembly, an amplifier, and an analog-to-digital system. As discussed above, each microphone (e.g., audio acquisition devices 202, 204, 206, 208, 210, 212, 214, 216, 218) may have imperfections and/or mismatch in the configuration or operation of each microphone. For example, each microphone of microphone array 200 may include various physical characteristics that impact the ability of each microphone to process speech signals. In some implementations, the combination of the microphone assembly, the amplifier, the analog-to-digital system, and/or an enclosure of the microphone may change the inter-microphone gain associated with signals received by microphone array 200.

For example, suppose that microphone 202 introduces a e.g., two decibel gain relative to the other microphones while microphone 212 introduces a e.g., one decibel gain relative to the other microphones. In this example, the inter-microphone gain mismatch may result in erroneous or inaccurate signal processing by a speech processing system (e.g., speech processing system 300). Accordingly, data augmentation process 10 may perform 402 augmentations to existing training data and/or signals received 400 from various microphones to generate inter-microphone gain-augmented signals. These inter-microphone gain-augmented signals may be used to train speech processing system 300 to account for gain mismatches between microphones of microphone array 200.

In some implementations, data augmentation process 10 may receive 400 a signal from each microphone of a plurality of microphones, thus defining a plurality of signals. Referring again to FIG. 5 and in some implementations, microphone array 200 may process speech (e.g., audio encounter information 106A-106C) from various sources. Accordingly, microphones 202, 204, 206, 208, 210, 212, 214, 216, 218 may generate signals (e.g., plurality of signals 500) representative of the speech processed by microphone array 200. In some implementations, data augmentation process 10 may receive 400 a signal from some or each of microphones 202, 204, 206, 208, 210, 212, 214, 216, 218.

In some implementations, data augmentation process 10 may perform 402 one or more inter-microphone gain-based augmentations on the plurality of signals, thus defining one or more inter-microphone gain-augmented signals. An inter-microphone gain-based augmented signal may generally include an augmentation of the gain of a signal or training data that represents variability in or imperfections associated with the relative gain levels between microphones of a microphone array. As discussed above, the inter-microphone gain-based augmented signal may allow a speech processing system (e.g., speech processing system 300) to account for mismatch or variations between microphone gain levels without requiring the expensive and complex signal compensation techniques used in conventional speech processing systems with microphone arrays.

In some implementations, performing 402 the one or more inter-microphone gain-based augmentations on the plurality of signals may include applying 404 a gain level from a plurality of gain levels to the signal from each microphone. Referring again to FIG. 5 and in some implementations, data augmentation process 10 may apply 404 a plurality of gain levels (e.g., plurality of gain levels 502) to the plurality of signals (e.g., plurality of signals 500). In some implementations, the plurality of signals 500 received 400 from the plurality of microphones (e.g., microphone array 200) may be received at any time prior to performing 402 the one or more inter-microphone gain-based augmentations. For example, plurality of signals 500 may include training data generated using microphone array 200. In some implementations, plurality of signals may include signals received 400 during real-time processing of speech signals. In this manner, the plurality of signals may be used to perform 402 inter-microphone gain-based augmentations at any time relative to when the plurality of signals are received.

In some implementations, the plurality of gain levels may be associated with particular microphones or a particular microphone array. For example, suppose a speaker is speaking in a conference room with a microphone array of a telephonic conferencing system deployed within the conference room. In this example, the properties of the microphones of the microphone array may introduce inter-microphone gain-based variations in the speech signal processed by the microphone array. Now suppose the speaker addresses a virtual assistant within a separate computing device. In this example, while the environmental features remain the same (i.e., the conference room), the microphone array of the virtual assistant may have factors and characteristics that may impact the signal processing differently than the microphone array of the telephonic conferencing system. In some implementations, the distinctions between microphone arrays may have various impacts on the performance of speech processing systems. Accordingly, data augmentation process 10 may allow speech signals received by one microphone array to be used in the training of speech processing systems with other microphone arrays and/or for adapting a speech processing system or model with new adaptation data.

In some implementations, data augmentation process 10 may receive a selection of a target microphone array. A target microphone array may include a type of microphone or microphone array. In some implementations, data augmentation process 10 may receive a selection of a target microphone array by providing particular inter-microphone gain-based characteristics associated with the target microphone array. In some implementations, data augmentation process 10 may utilize a graphical user interface for receiving a selection of a target microphone array from a library of target microphone arrays. In one example, data augmentations process 10 may receive selections (e.g., via a graphical user interface) of various characteristics of the microphone array (e.g., a type of microphone array, an arrangement of microphones in a microphone array, etc.) to define a target microphone array. As will be discussed in greater detail below and in some implementations, data augmentation process 10 may receive a range or distribution of characteristics for the target microphone array. While an example of a graphical user interface has been described, it will be appreciated that a target microphone array may be selected in various ways within the scope of the present disclosure (e.g., manually by a user, automatically by data augmentation process 10, a pre-defined target microphone array, etc.).

In some implementations, data augmentation process 10 may perform 402 one or more inter-microphone gain-based augmentations on the plurality of signals based upon, at least in part, a target microphone array. As will be discussed in greater detail below, it may be desirable to augment a plurality of signals associated with a particular microphone array for various reasons. For example and in some implementations, data augmentation process 10 may perform one or more inter-microphone gain-based augmentations on the plurality of signals to utilize the plurality of signals for training a speech processing system with a target microphone array. In this example, data augmentation process 10 may train a speech processing system with speech signals received by a different microphone array which may allow for speech processing systems to be effectively utilized with various microphone arrays using an augmented set of training signals.

In another example, data augmentation process 10 may perform 402 one or more inter-microphone gain-based augmentations on the plurality of signals to generate additional training data for speech processing systems with varying levels of gain mismatch or variation among the same or similar types of microphone arrays. In this manner, data augmentation process 10 may train speech processing systems to be more robust against variations in gain by augmenting a set of training data with various gain levels representative of the imperfections in the microphones of the microphone array. While two examples have been provided for utilizing inter-microphone gain-augmented signals, it will be appreciated that data augmentation process 10 may perform inter-microphone gain-based augmentations on the plurality of signals for various other purposes within the scope of the present disclosure. For example and in some implementations, inter-microphone gain-based augmentations may be used to adapt a speech processing system with new adaptation data (e.g., inter-microphone gain-based augmentations).

In some implementations, the plurality of gain levels to be applied to the plurality of signals may be simulated using one or more machine learning models. For example, a plurality of gain levels for a microphone array may be simulated using one or more machine learning models configured to "learn" how the characteristics of a microphone array or individual microphones impact the gain level of signals received from the microphone array. As is known in the art, a machine learning model may generally include an algorithm or combination of algorithms that has been trained to recognize certain types of patterns. For example, machine learning approaches may be generally divided into three categories, depending on the nature of the signal available: supervised learning, unsupervised learning, and reinforcement learning. As is known in the art, supervised learning may include presenting a computing device with example inputs and their desired outputs, given by a "teacher", where the goal is to learn a general rule that maps inputs to outputs. With unsupervised learning, no labels are given to the learning algorithm, leaving it on its own to find structure in its input. Unsupervised learning can be a goal in itself (discovering hidden patterns in data) or a means towards an end (feature learning). As is known in the art, reinforcement learning may generally include a computing device interacting in a dynamic environment in which it must perform a certain goal (such as driving a vehicle or playing a game against an opponent). As it navigates its problem space, the program is provided feedback that's analogous to rewards, which it tries to maximize. While three examples of machine learning approaches have been provided, it will be appreciated that other machine learning approaches are possible within the scope of the present disclosure. Accordingly, data augmentation process 10 may utilize a machine learning model (e.g., machine learning model 302) to simulate how the characteristics of a microphone array or individual microphones impact the gain level of signals received from the microphone array.

In some implementations, the plurality of gain levels to be applied 404 to the plurality of signals may be measured from one or more microphone arrays. For example and as discussed above, data augmentation process 10 may receive a plurality of signals from a microphone array. In some implementations, data augmentation process 10 may determine the gain levels for each microphone of the microphone array. For example, data augmentation process 10 may define a range of gain levels for the microphone array (e.g., for each microphone and/or for the microphone array generally). As will be discussed in greater detail below, data augmentation process 10 may define a distribution of gain levels for the microphone array (e.g., for each microphone and/or for the microphone array generally). In some implementations, the distribution of gain levels may be a function of frequency such that different gain levels are observed as a function of frequency for a particular microphone and/or for the microphone array generally.

In some implementations, applying 404 the gain level from the plurality of gain levels to the signal from each microphone may include applying 406 a gain level, from a predefined range of gain levels, to the signal from each microphone. For example, the predefined range of gain levels may include a maximum gain level and a minimum gain level. In one example, the predefined range of gain levels may be a default range of gain levels. In another example, the predefined range of gain levels may be determined from a set of training data for a particular microphone array. In another example, the predefined range of gain levels may be manually defined (e.g., by a user via a user interface). While several examples have been described of how the range of gain levels may be defined, it will be appreciated that the predefined range of gain levels may be defined in various ways within the scope of the present disclosure.

Continuing with the above example, suppose that microphone 202 introduces a e.g., two decibel gain relative to the other microphones while microphone 212 introduces a e.g., one decibel gain relative to the other microphones of microphone array 200 despite the fact that microphones 202, 204, 206, 208, 210, 212, 214, 216, 218 are identical. In this example, data augmentation process 10 may define the predefined range of gain levels as e.g., zero decibels to e.g., two decibels. Data augmentation process 10 may apply 406 gain levels 502 ranging from e.g., zero decibels to e.g., two decibels to each signal from each of microphones 202, 204, 206, 208, 210, 212, 214, 216, 218. Accordingly, data augmentation process 10 may perform 402 one or more inter-microphone gain-based augmentations on each signal by applying 406 the plurality of gain levels of the predefined range of gain levels to the signals of each microphone to generate inter-microphone gain-augmented signals 504.

In some implementations, applying 404 the gain level from the plurality of gain levels to the signal from each microphone may include applying 408 a random gain level, from the predefined range of gain levels, to the signal from each microphone. For example, data augmentation process 10 may apply a randomly selected gain level from the predefined range of gain levels to the signals of each microphone to generate the one or more inter-microphone gain-augmented signals (e.g., inter-microphone gain-augmented signals 504).

In some implementations, the gain variations may be controlled via a parameter that specifies the maximum and minimum variation across microphones. For example, data augmentation process 10 may receive a selection of a gain level variation parameter (e.g., from a user via a user interface) to define the maximum and/or minimum variation of the gain levels across the plurality of microphones. For example, the gain level variation parameter may include a distribution of gain levels. In some implementations, the gain level variation parameter may include random variations in gain levels, gain level variations according to Gaussian distribution, gain level variations according to Poisson distribution, and/or gain level variations configured to be learned by a machine learning model. Accordingly, it will be appreciated that the gain level variation parameter may include any type of distribution of gain levels from which gain levels may be applied to the one or more signals. In some implementations, the gain level variation parameter may include a default gain level variation parameter defined for a particular microphone array or type of microphone. In this manner, data augmentation process 10 may limit the variation of the gain levels for the one or more inter-microphone gain-augmented signals.

Figure 6:
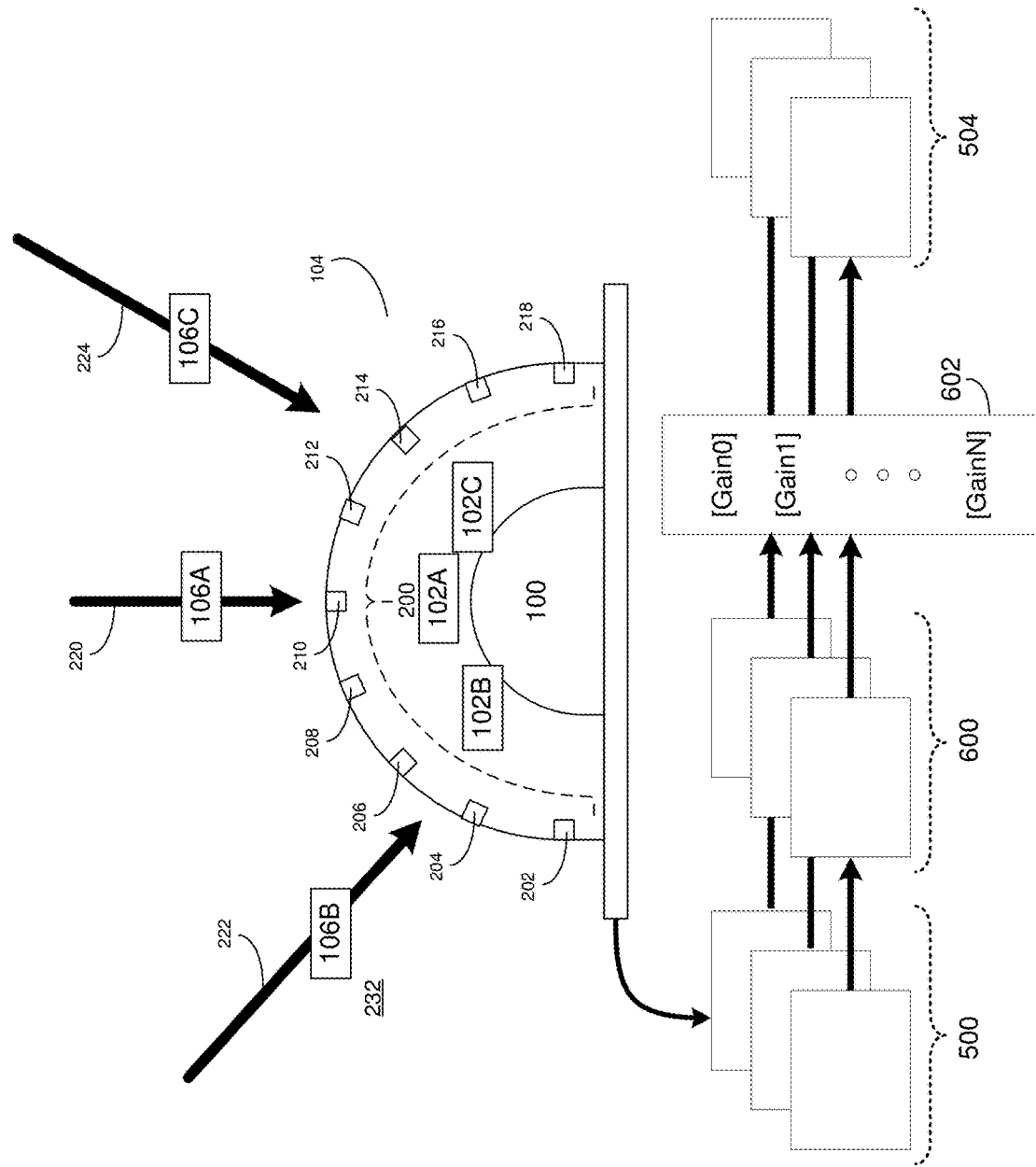

In some implementations, performing 402 the one or more inter-microphone gain-based augmentations on the one or more signals may include converting 410 the one or more signals to the frequency domain. Referring also to FIG. 6 and in some implementations, data augmentation process 10 may convert 410 the plurality of signals received from the plurality of microphones (e.g., plurality of microphones 202, 204, 206, 208, 210, 212, 214, 216, 218) to frequency domain representations of the signals (e.g., plurality of frequency domain-based signals 600). In some implementations, converting 410 the one or more signals to the feature domain may include obtaining frequency components from the signal. In some implementations, data augmentation process 10 may obtain the frequency components from the signal by applying a Short-Time Fourier Transform (STFT) to the signal. While a STFT is discussed as a way of obtaining frequency components from the signal, it will be appreciated that other transformations may be used to derive the frequency components from the signal and/or to convert a time domain representation of a signal into a frequency domain representation of the signal within the scope of the present disclosure.

In some implementations, performing 402 the one or more inter-microphone gain-based augmentations on the one or more signals may include applying 412 a plurality of gain levels to a plurality of frequency bands of the one or more signals converted to the frequency domain. For example, the gain level variability for a microphone array may be frequency dependent. In some implementations, data augmentation process 10 may define a plurality of gain levels for a plurality of frequency bands. For instance, data augmentation process 10 may define a vector of gain levels for various frequency bands (e.g., gain level vector 602). In this example, each entry of gain level vector 602 may correspond to a particular frequency or frequency band. In some implementations, data augmentation process 10 may apply 412 the same gain level to each frequency band or may apply 412 different gain levels to each frequency band of each microphone signal of the plurality of signals received from the microphone array.

In some implementations, performing 402 the one or more inter-microphone gain-based augmentations on the one or more signals may include one or more of amplifying 414 at least a portion of the one or more signals and attenuating 416 at least a portion of the one or more signals. For example, suppose that gain level vector 602 specifies a gain level of greater than one for a particular frequency band. In this example, data augmentation process 10 may amplify 414 the frequency band of the signals from each microphone by the gain level. In another example, suppose that gain level vector 602 specifies a gain level of less than one for another frequency band. In this example, data augmentation process 10 may attenuate 416 the frequency band of the signals from each microphone by the gain level. Accordingly, data augmentation process 10 may perform 402 the one or more inter-microphone gain-based augmentations on the one or more signals by amplifying 414 and/or attenuating 416 the signal for each microphone of the microphone array. In this manner, data augmentation process 10 may augment training data to account for or represent inter-microphone gain level mismatch between microphones of a microphone array.

Figure 7:
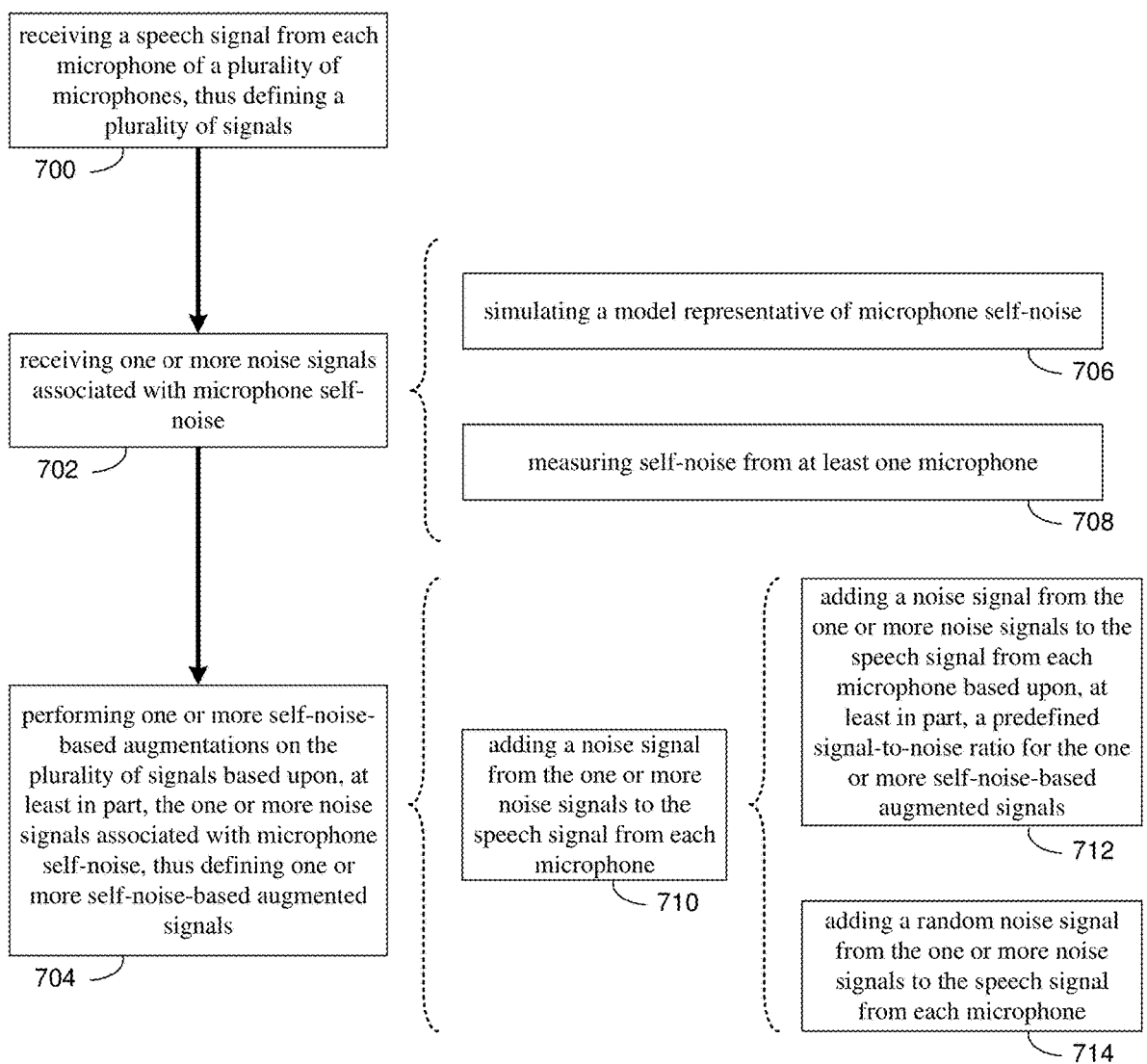
FIG. 7 is a flow chart of one implementation of the data augmentation process of FIG. 1.

As discussed above and referring also at least to FIGS. 7-8, data augmentation process 10 may receive 700 a speech signal from each microphone of a plurality of microphones, thus defining a plurality of signals. One or more noise signals associated with microphone self-noise may be received 702. One or more self-noise-based augmentations may be performed 704 on the plurality of signals based upon, at least in part, the one or more noise signals associated with microphone self-noise, thus defining one or more self-noise-based augmented signals.

Figure 8:
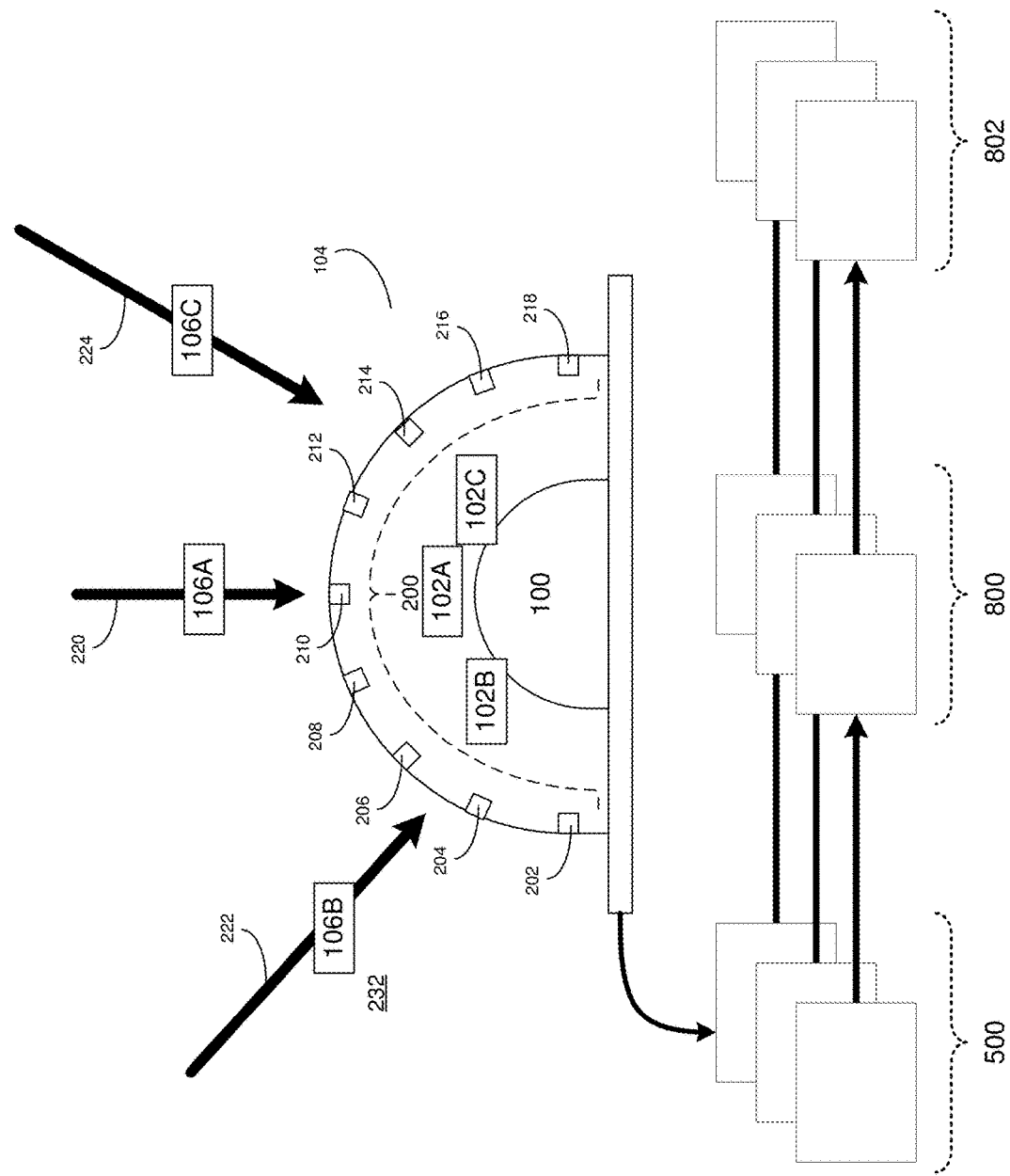
FIG. 8 is a diagrammatic view of a modular ACD system according to one implementation of the data augmentation process of FIG. 1.

Referring also to FIG. 8 and in some implementations, audio recording system 104 may include directional microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. In some implementations, each audio acquisition device or microphone may include a microphone assembly, an amplifier, and/or an analog-to-digital system. As discussed above, each microphone (e.g., audio acquisition devices 202, 204, 206, 208, 210, 212, 214, 216, 218) may have imperfections and/or mismatch in the configuration or operation of each microphone. For example, each microphone of microphone array 200 may include various physical characteristics that impact the ability of each microphone to process speech signals. In some implementations, the combination of the microphone assembly, the amplifier, and/or the analog-to-digital system may introduce microphone "self-noise" associated with signals received by microphone array 200. As discussed above, "self-noise" may refer to the amount of noise output by a microphone when positioned in an environment without external noises. The spectral shape of this noise may impact some frequencies or frequency bands more than others and different microphones may have different self-noise levels or characteristics.

For example, suppose that microphone 204 outputs a first noise signal while microphone 214 outputs a second noise signal. In this example, the self-noise signals output by each microphone may result in erroneous or inaccurate signal processing by a speech processing system (e.g., speech processing system 300). Accordingly, data augmentation process 10 may perform 704 augmentations to existing training data and/or signals received 700 from various microphones to generate microphone self-noise-based augmentations of the signals. These microphone self-noise-based augmented signals may be used to train speech processing system 300 to account for self-noise output by particular microphones of microphone array 200.

In some implementations, data augmentation process 10 may receive 700 a signal from each microphone of a plurality of microphones, thus defining a plurality of signals. Referring again to FIG. 8 and in some implementations, microphone array 200 may process speech (e.g., audio encounter information 106A-106C) from various sources. Accordingly, microphones 202, 204, 206, 208, 210, 212, 214, 216, 218 may generate signals (e.g., plurality of signals 500) representative of the speech processed by microphone array 200. In some implementations, data augmentation process 10 may receive 700 a signal from some or each of microphones 202, 204, 206, 208, 210, 212, 214, 216, 218.

In some implementations, data augmentation process 10 may receive 702 one or more noise signals associated with microphone self-noise. As discussed above and in some implementations, each microphone may output a noise signal in the absence of any external noises. The characteristics of the output noise signal or microphone self-noise may be based upon the electromechanical properties of the microphone assembly, the amplifier, and/or the analog-to-digital system. Referring again to FIG. 8, data augmentation process 10 may receive 702 one or more noise signals associated with microphone self-noise (e.g., one or more noise signals 800) from various sources (e.g., one or more machine learning models, a measurement of a microphone deployed in a noiseless environment, etc.).

In some implementations, receiving 702 the one or more noise signals associated with microphone self-noise may include simulating 706 a model representative of microphone self-noise. For example, the one or more noise signals may be simulated using one or more machine learning models configured to "learn" how the characteristics of a microphone array or individual microphones generate noise. As discussed above and as known in the art, a machine learning model may generally include an algorithm or combination of algorithms that has been trained to recognize certain types of patterns. In some implementations, a machine learning model (e.g., machine learning model 302) may be configured to simulate the operation of a microphone to generate the one or more noise signals associated with microphone self-noise (e.g., one or more noise signals 800).

In some implementations, receiving 702 the one or more noise signals associated with microphone self-noise may include measuring 708 self-noise from at least one microphone. For example and as discussed above, data augmentation process 10 may receive a plurality of signals from a microphone array. In some implementations, data augmentation process 10 may determine the self-noise for each microphone of the microphone array (e.g., one or more noise signals 800). For example, data augmentation process 10 may define a distribution of self-noise signals for the microphone array (e.g., for each microphone and/or for the microphone array generally). In some implementations, the distribution of self-noise signals may be a function of frequency such that different noise responses are observed as a function of frequency for a particular microphone and/or for the microphone array generally.

In some implementations, data augmentation process 10 may perform 704 one or more self-noise-based augmentations on the plurality of signals based upon, at least in part, the one or more noise signals associated with microphone self-noise, thus defining one or more self-noise-based augmented signals. A self-noise-based augmented signal may generally include an augmentation of a signal or training data to include noise representative of the self-noise generated by a microphone. As discussed above, the self-noise-based augmented signal may allow a speech processing system (e.g., speech processing system 300) to account for self-noise output by a microphone without requiring the expensive and complex signal compensation techniques used in conventional speech processing systems with microphone arrays.

In some implementations, the one or more noise signals may be associated with particular microphones or a microphone array. For example, suppose a speaker is speaking in a clinical environment with a microphone array of modular ACD system 54 deployed within the clinical environment. In this example, the properties of the microphones of the microphone array may output various noise signals or noise signal distributions in the speech signal processed by the microphone array. Now suppose the speaker addresses a virtual assistant within a separate computing device positioned within the clinical environment. In this example, while the environmental features remain the same (i.e., the clinical environment), the microphone array of the virtual assistant may have factors and characteristics that may impact the signal processing differently than the microphone array of modular ACD system 54. In some implementations, the distinctions between microphone arrays may have various impacts on the performance of speech processing systems. Accordingly, data augmentation process 10 may allow speech signals received by one microphone array to be used in the training of speech processing systems with other microphone arrays and/or for adapting a speech processing system or model with new adaptation data.

In some implementations, data augmentation process 10 may receive a selection of a target microphone array. A target microphone array may include a type of microphone or microphone array. In some implementations, data augmentation process 10 may receive a selection of a target microphone array by providing particular self-noise characteristics associated with the target microphone array. In some implementations, data augmentation process 10 may utilize a graphical user interface for receiving a selection of a target microphone array from a library of target microphone arrays. In one example, data augmentations process 10 may receive selections (e.g., via a graphical user interface) of various characteristics of the microphone array (e.g., a type of microphone array, an arrangement of microphones in a microphone array, etc.) to define a target microphone array. As will be discussed in greater detail below and in some implementations, data augmentation process 10 may receive a range or distribution of characteristics for the target microphone array. While an example of a graphical user interface has been described, it will be appreciated that a target microphone array may be selected in various ways within the scope of the present disclosure (e.g., manually by a user, automatically by data augmentation process 10, a pre-defined target microphone array, etc.).

In some implementations, data augmentation process 10 may perform 704 one or more self-noise-based augmentations on the plurality of signals based upon, at least in part, a target microphone array. As will be discussed in greater detail below, it may be desirable to augment a plurality of signals associated with a particular microphone array for various reasons. For example and in some implementations, data augmentation process 10 may perform one or more self-noise-based augmentations on the plurality of signals to utilize the plurality of signals for training a speech processing system with a target microphone array. In this example, data augmentation process 10 may train a speech processing system with speech signals received by a different microphone array which may allow for speech processing systems to be effectively utilized with various microphone arrays using an augmented set of training signals.

In another example, data augmentation process 10 may perform 704 one or more self-noise-based augmentations on the plurality of signals to generate additional training data for speech processing systems with varying self-noise among the same or similar types of microphones or microphone arrays. In this manner, data augmentation process 10 may train speech processing systems to be more robust against microphone self-noise by augmenting a set of training data with self-noise signals representative of the imperfections in the microphones of the microphone array. While two examples have been provided for utilizing self-noise-based augmented signals, it will be appreciated that data augmentation process 10 may perform self-noise-based augmentations on the plurality of signals for various other purposes within the scope of the present disclosure. For example and in some implementations, self-noise-based augmentations may be used to adapt a speech processing system with new adaptation data (e.g., self-noise-based augmented signals).

In some implementations, performing 704 the one or more self-noise-based augmentations on the plurality of signals based upon, at least in part, the one or more noise signals associated with microphone self-noise may include adding 710 a noise signal from the one or more noise signals to the signal from each microphone. For example, suppose that data augmentation process 10 receives 702 a first noise signal associated with the self-noise of microphone 204 and a second noise signal associated with the self-noise of microphone 214. In this example, data augmentation process 10 may add the first noise signal associated with the self-noise of microphone 204 and the second noise signal associated with the self-noise of microphone 214 to the signal from each microphone of the plurality of signals (e.g., plurality of signals 500). Accordingly, data augmentation process 10 may generate one or more self-noise-based augmented signals for the signal from each microphone (e.g., self-noise-based augmented signals 802). In this manner, data augmentation process 10 may allow for training data to be generated with the self-noise of microphone 204 and self-noise of microphone 214. While an example of two self-noise signals for two microphones of microphone array 200 have been described, it will be appreciated that any number of self-noise signals for any number of microphones may be added to the signal from each microphone to generate one or more self-noise-based augmented signals within the scope of the present disclosure.

In some implementations, adding 710 a noise signal to the signal from each microphone may include adding 712 a noise signal from the one or more noise signals to the signal from each microphone based upon, at least in part, a predefined signal-to-noise ratio for the one or more self-noise-based augmented signals. For example, data augmentation process 10 may receive a selection of a signal-to-noise (SNR) ratio for the one or more self-noise-based augmented signals. In some implementations, the SNR ratio may be received as a selection of a SNR parameter (e.g., from a user via a user interface). In some implementations, the SNR parameter may include a default SNR parameter defined for a particular microphone array or type of microphone.

In some implementations, adding 710 a noise signal from the one or more noise signals to the signal from each microphone may include adding 714 a random noise signal from the one or more noise signals to the signal from each microphone. For example and as discussed above, data augmentation process 10 may receive one or more noise signals associated with microphone self-noise for one or more microphones of the microphone array. Continuing with the above example, suppose that data augmentation process 10 receives 702 a first noise signal associated with the self-noise of microphone 204 and a second noise signal associated with the self-noise of microphone 214. In this example, data augmentation process 10 may add 714 a random noise signal (e.g., the first noise signal and/or the second noise signal) to the signal from each microphone (e.g., signals from each of microphones 202, 204, 206, 208, 210, 212, 214, 216, 218). In this manner, data augmentation process 10 may generate more diverse training data for speech processing systems that allow the speech processing systems to be more robust against microphone self-noise of microphone assemblies of a microphone array.

Figure 9:
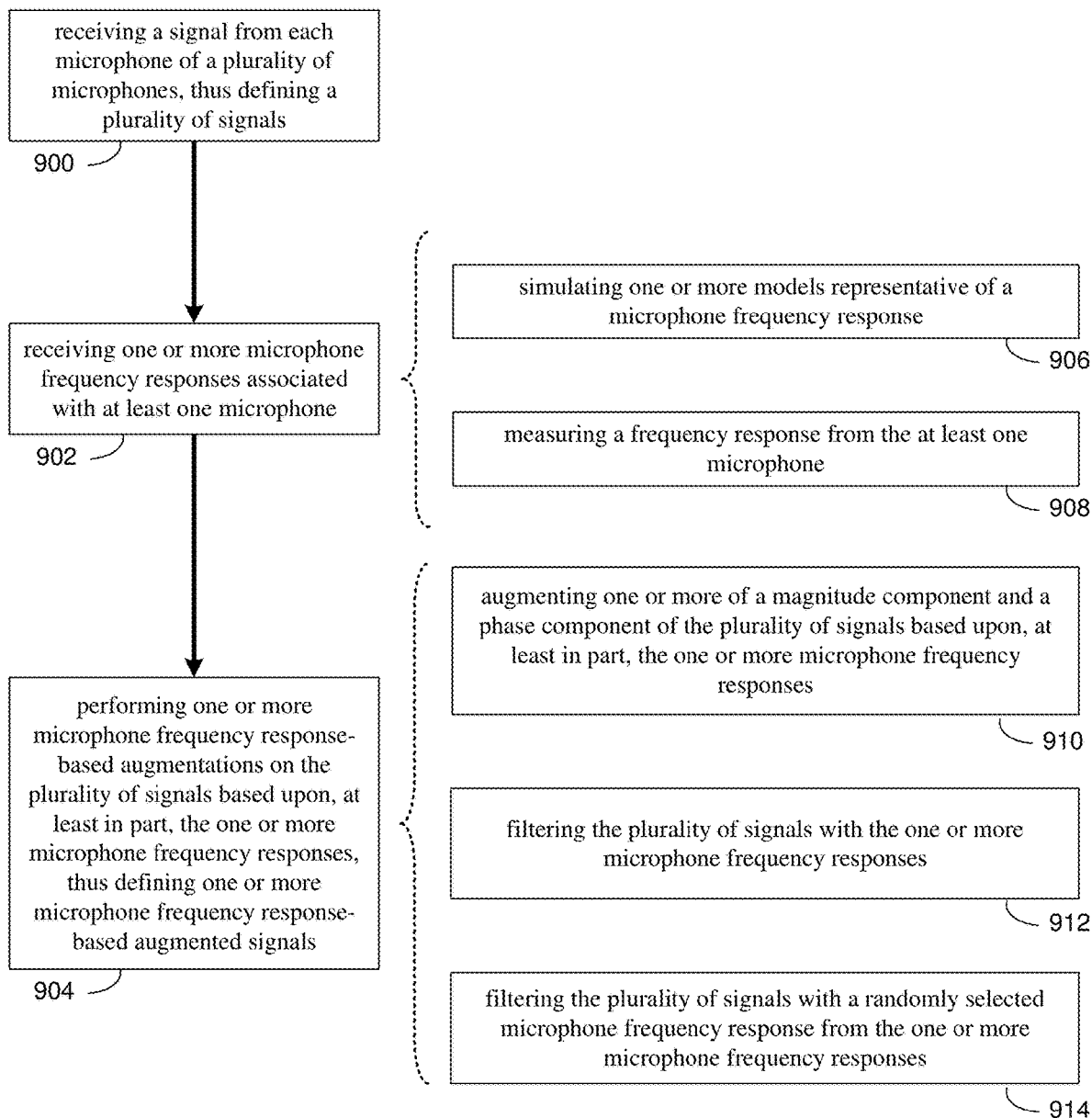
FIG. 9 is a flow chart of one implementation of the data augmentation process of FIG. 1.

As discussed above and referring also at least to FIGS. 9-11, data augmentation process 10 may receive 900 a signal from each microphone of a plurality of microphones, thus defining a plurality of signals. One or more microphone frequency responses associated with at least one microphone may be received 902. One or more microphone frequency response-based augmentations may be performed 904 on the plurality of signals based upon, at least in part, the one or more microphone frequency responses, thus defining one or more microphone frequency response-based augmented signals.

Figure 10:
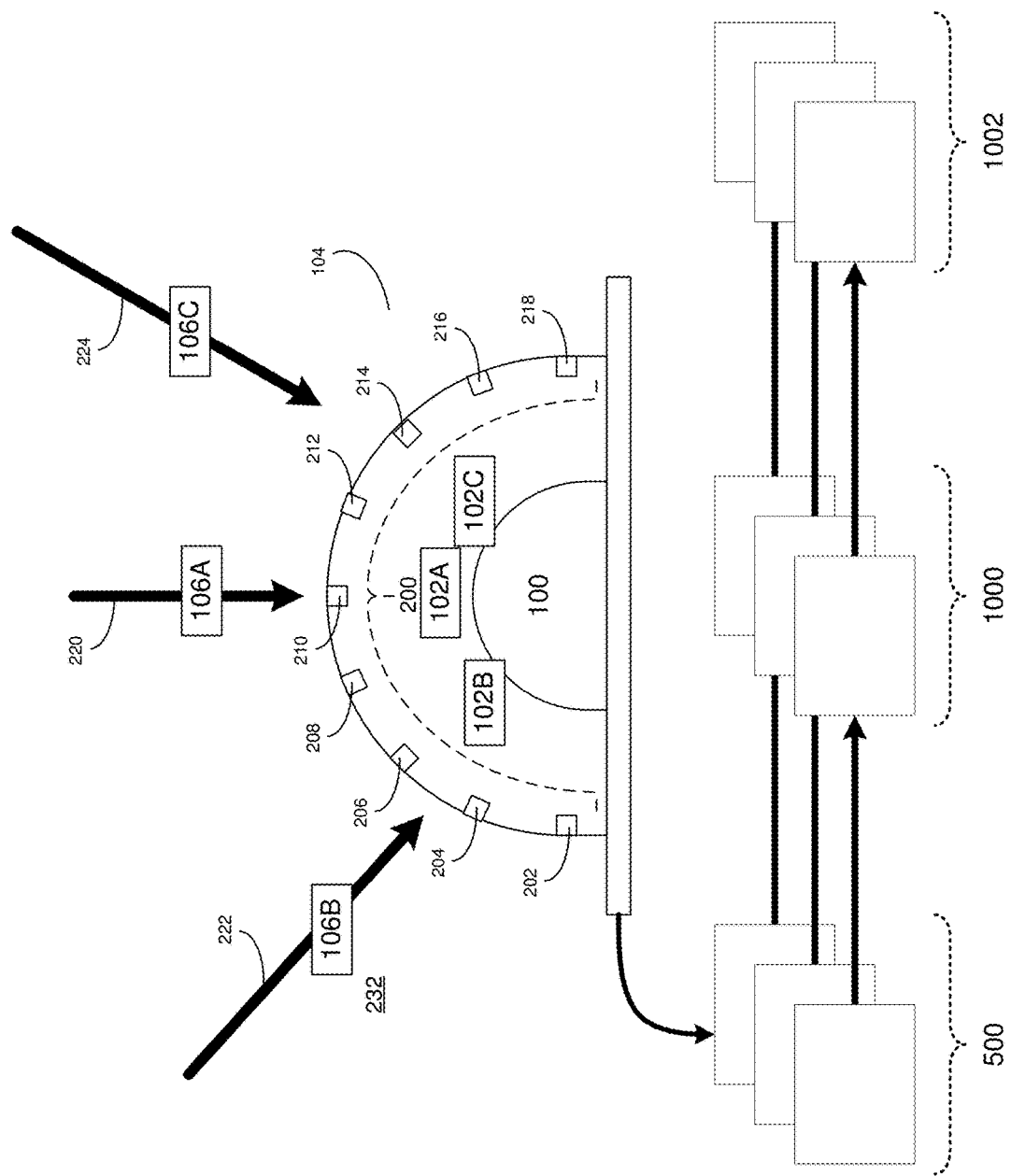
FIG. 10 is a diagrammatic view of a modular ACD system according to one implementation of the data augmentation process of FIG. 1.

Referring also to FIG. 10 and in some implementations, audio recording system 104 may include directional microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. In some implementations, each audio acquisition device or microphone may include a microphone assembly, an amplifier, and an analog-to-digital system. As discussed above, each microphone (e.g., audio acquisition devices 202, 204, 206, 208, 210, 212, 214, 216, 218) may have imperfections and/or mismatch in the configuration or operation of each microphone.

Figure 11:
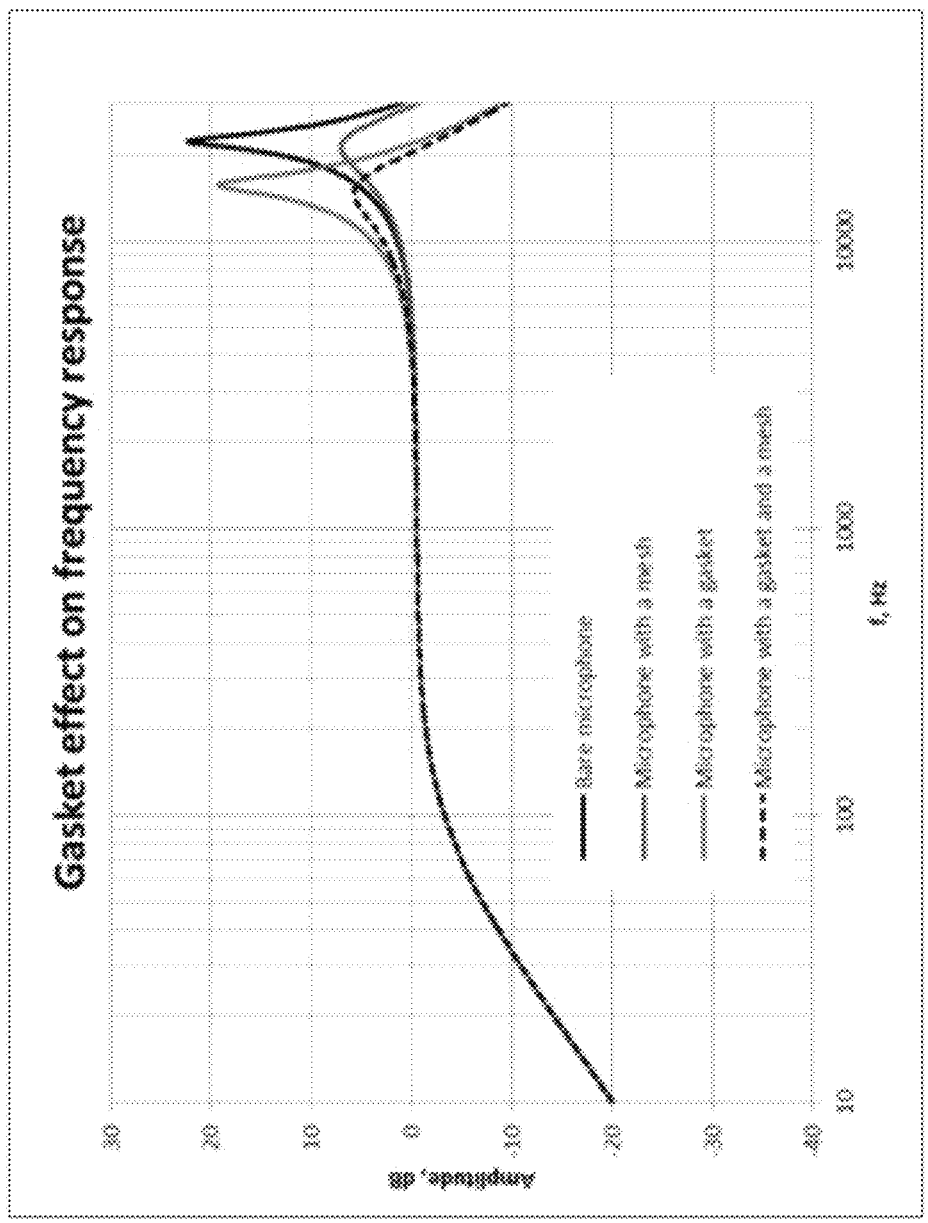
FIG. 11 is a diagrammatic view of a microphone frequency response according to one implementation of the data augmentation process of FIG. 1.

For example, each microphone of microphone array 200 may include various physical characteristics that impact the ability of each microphone to process speech signals. In some implementations, the combination of the microphone assembly, the amplifier, the analog-to-digital system, and/or the enclosure of each microphone may introduce a microphone frequency response. In some implementations, a microphone frequency response may refer to a non-flat frequency response in terms of magnitude and a non-linear frequency response in terms of phase that indicates a change in microphone sensitivity at different frequencies. Typical MEMS microphones exhibit a non-flat frequency response shape. For example, a microphone enclosure may also introduce spectral shaping to the microphone frequency response. Referring also to FIG. 11 and in some implementations, a microphone frequency response may vary as a function of various types of coverings or gaskets applied to a microphone. Accordingly, it will be appreciated that a microphone's frequency response may include variations in signal magnitude and/or phase for different physical characteristics of the microphone. In some implementations, varying microphone frequency responses of one or more microphones of a microphone array may result in erroneous processing of speech signals by speech processing systems.

For example, suppose that microphone 206 is characterized by a first microphone frequency response while microphone 216 is characterized by a second frequency response. In this example, the microphone frequency responses produced by each microphone may result in erroneous or inaccurate signal processing by a speech processing system (e.g., speech processing system 300). Accordingly, data augmentation process 10 may perform 904 augmentations to existing training data and/or signals received 900 from various microphones to generate microphone frequency response-based augmented signals. These microphone frequency response-based augmented signals may be used to train speech processing system 300 to account for frequency responses generated by particular microphones of microphone array 200.

In some implementations, data augmentation process 10 may receive 900 a signal from each microphone of a plurality of microphones, thus defining a plurality of signals. Referring again to FIG. 10 and in some implementations, microphone array 200 may process speech (e.g., audio encounter information 106A-106C) from various sources. Accordingly, microphones 202, 204, 206, 208, 210, 212, 214, 216, 218 may generate signals (e.g., plurality of signals 500) representative of the speech processed by microphone array 200. In some implementations, data augmentation process 10 may receive 900 a signal from some or each of microphones 202, 204, 206, 208, 210, 212, 214, 216, 218.

In some implementations, data augmentation process 10 may receive 902 one or more microphone frequency responses associated with at least one microphone. As discussed above and in some implementations, each microphone may generate a frequency response based upon the physical characteristics of the microphone. The shape of the microphone frequency response (e.g., in terms of magnitude and phase) may be based upon the electromechanical properties of the microphone assembly, the amplifier, the analog-to-digital system, and/or an enclosure of the microphone. Referring again to FIG. 10, data augmentation process 10 may receive 902 one or more microphone frequency responses associated with at least one microphone (e.g., one or more microphone frequency responses 1000) from various sources (e.g., one or more machine learning models, from the measurement of a frequency response of at least one microphone, etc.).

In some implementations, receiving 902 the one or more frequency responses associated with the at least one microphone may include simulating 906 one or more models representative of a microphone frequency response. For example, the one or more microphone frequency responses may be simulated using one or more machine learning models configured to "learn" the frequency response of individual microphones. As discussed above and as known in the art, a machine learning model may generally include an algorithm or combination of algorithms that has been trained to recognize certain types of patterns. In some implementations, a machine learning model (e.g., machine learning model 302) may be configured to simulate the operation of a microphone to generate the one or more frequency responses (e.g., one or more microphone frequency responses 1000).

In some implementations, receiving 902 the one or more frequency responses associated with the at least one microphone may include measuring 908 a frequency response from the at least one microphone. For example and as discussed above, data augmentation process 10 may receive a plurality of signals from a microphone array. In some implementations, data augmentation process 10 may determine the frequency response for each microphone of the microphone array. For example, data augmentation process 10 may define a distribution of frequency responses for the microphone array (e.g., for each microphone and/or for the microphone array generally).

In some implementations, data augmentation process 10 may perform 904 one or more microphone frequency response-based augmentations on the plurality of signals based upon, at least in part, the one or more microphone frequency responses, thus defining one or more microphone frequency response-based augmented signals. A microphone frequency response-based augmented signal may generally include an augmentation of a signal or training data to include augmentations in the phase and/or magnitude of the signal or training data as a function of frequency. As discussed above, the microphone frequency response-based augmented signal may allow a speech processing system (e.g., speech processing system 300) to account for phase and/or magnitude variations as a function of frequency for a microphone without requiring the expensive and complex signal compensation techniques used in conventional speech processing systems with microphone arrays.

In some implementations, the one or more microphone frequency responses may be associated with particular microphones or a microphone array. For example, suppose a speaker is speaking in a clinical environment with a microphone array of modular ACD system 54 deployed within the clinical environment. In this example, the properties of the microphones of the microphone array may generate various frequency responses. Now suppose the speaker addresses a virtual assistant within a separate computing device positioned within the clinical environment. In this example, while the environmental features remain the same (i.e., the clinical environment), the microphone array of the virtual assistant may have factors and characteristics that may impact the signal processing differently than the microphone array of modular ACD system 54. In some implementations, the distinctions between microphone arrays may have various impacts on the performance of speech processing systems. Accordingly, data augmentation process 10 may allow speech signals received by one microphone array to be used in the training of speech processing systems with other microphone arrays and/or for adapting a speech processing system or model with new adaptation data.

In some implementations, data augmentation process 10 may receive a selection of a target microphone or microphone array. A target microphone or microphone array may include a type of microphone or microphone array. In some implementations, data augmentation process 10 may receive a selection of a target microphone or microphone array by providing a particular frequency response associated with the target microphone or microphone array. In some implementations, data augmentation process 10 may utilize a graphical user interface for receiving a selection of a target microphone array from a library of target microphone arrays. In one example, data augmentation process 10 may receive selections (e.g., via a graphical user interface) of various characteristics of the microphone array (e.g., a type of microphone array, an arrangement of microphones in a microphone array, etc.) to define a target microphone array. As will be discussed in greater detail below and in some implementations, data augmentation process 10 may receive a range or distribution of characteristics for the target microphone array. While an example of a graphical user interface has been described, it will be appreciated that a target microphone array may be selected in various ways within the scope of the present disclosure (e.g., manually by a user, automatically by data augmentation process 10, a pre-defined target microphone array, etc.).

In some implementations, data augmentation process 10 may perform 904 one or more microphone frequency response-based augmentations on the plurality of signals based upon, at least in part, a target microphone or microphone array. As will be discussed in greater detail below, it may be desirable to augment a plurality of signals associated with a particular microphone array for various reasons. For example and in some implementations, data augmentation process 10 may perform one or more microphone frequency response-based augmentations on the plurality of signals to utilize the plurality of signals for training a speech processing system with a target microphone array. In this example, data augmentation process 10 may train a speech processing system with speech signals received by a different microphone array which may allow for speech processing systems to be effectively utilized with various microphone arrays using an augmented set of training signals.

In another example, data augmentation process 10 may perform 904 one or more microphone frequency response-based augmentations on the plurality of signals to generate additional training data for speech processing systems with varying frequency responses among the same or similar types of microphone arrays. In this manner, data augmentation process 10 may train speech processing systems to be more robust against variations in frequency responses by augmenting a set of training data with various frequency responses or frequency response distributions. While two examples have been provided for utilizing microphone frequency response-based augmented signals, it will be appreciated that data augmentation process 10 may perform microphone frequency response-based augmentations on the plurality of signals for various other purposes within the scope of the present disclosure. For example and in some implementations, frequency response-based augmentations may be used to adapt a speech processing system with new adaptation data (e.g., microphone frequency response-based augmentations).

In some implementations, performing 904 the one or more microphone frequency response-based augmentations on the plurality of signals based upon, at least in part, the one or more microphone frequency responses may include augmenting 910 one or more of a magnitude component and a phase component of the plurality of signals based upon, at least in part, the one or more microphone frequency responses. As discussed above and in some implementations, each signal may include magnitude and phase components. Continuing with the above example, suppose that microphone 206 outputs a first microphone frequency response while microphone 216 outputs a second frequency response. In this example, data augmentation process 10 may augment signals from each microphone (e.g., microphones 202, 204, 206, 208, 210, 212, 214, 216, 218) with magnitude and/or phase components of the first microphone frequency response associated with microphone 206 and/or the second microphone frequency response associated with microphone 216.

In some implementations, performing 904 the one or more microphone frequency response-based augmentations on the plurality of signals based upon, at least in part, the one or more microphone frequency responses may include filtering 912 the plurality of signals with the one or more microphone frequency responses. For example, data augmentation process 10 may filter each of the microphone signals from the plurality of signals (e.g., plurality of signals 500) with the one or more microphone frequency responses (e.g., one or more microphone frequency responses 1000). As is known in the art, filtering signals may include convolving the signals in the time domain and multiplying the signals in the frequency domain. For example, convolution of signals is a mathematical way of combining two signals to form a third signal and convolving signals in the time domain is equivalent to multiplying the spectra of the signals in the frequency domain. In some implementations, filtering 912 the plurality of signals (e.g., plurality of signals 500) with the one or more microphone frequency responses (e.g., one or more microphone frequency responses 1000) may generate one or more microphone frequency response-based augmented signals (e.g., one or more microphone frequency response-based augmented signals 1002).

Continuing with the above example, data augmentation process 10 may perform 904 the one or more microphone frequency response-based augmentations on the plurality of signals based upon, at least in part, the one or more microphone frequency responses by filtering 912 the plurality of signals 500 with the microphone frequency response associated with microphone 206 to generate one or more microphone frequency response-based augmented signals 1002. In this example, the filtering of the plurality of signals 500 with the microphone frequency response associated with microphone 206 may generate magnitude and/or phase augmentations or variations of the plurality of signals. In this manner, data augmentation process 10 may generate augmented signals (e.g., one or more microphone frequency response-based augmented signals 1002) that allow speech processing systems to account for the frequency response of specific microphones when processing speech signals.

In some implementations, performing 904 the one or more microphone frequency response-based augmentations on the plurality of signals based upon, at least in part, the one or more microphone frequency responses may include filtering 914 the plurality of signals with a randomly selected microphone frequency response from the one or more microphone frequency responses. For example, data augmentation process 10 may perform 904 the one or more microphone frequency response-based augmentations on the plurality of signals based upon, at least in part, the one or more microphone frequency responses by filtering 914 the plurality of signals 500 with randomly-selected magnitude and/or phase components from one or more microphone frequency responses 1000. In this example, data augmentation process 10 may randomly select magnitude and/or phase components from the microphone frequency response associated with microphone 206 and/or the microphone frequency response associated with microphone 216 to filter 914 with the microphone signals from plurality of signals 500. While an example of e.g., two frequency responses has been provided, it will be appreciated that data augmentation process 10 may perform 904 the one or more microphone frequency response-based augmentations on the plurality of signals based upon, at least in part, the one or more microphone frequency responses by filtering 914 the plurality of signals 500 with randomly-selected magnitude and/or phase components from any number of microphone frequency responses within the scope of the present disclosure.

Figure 12:
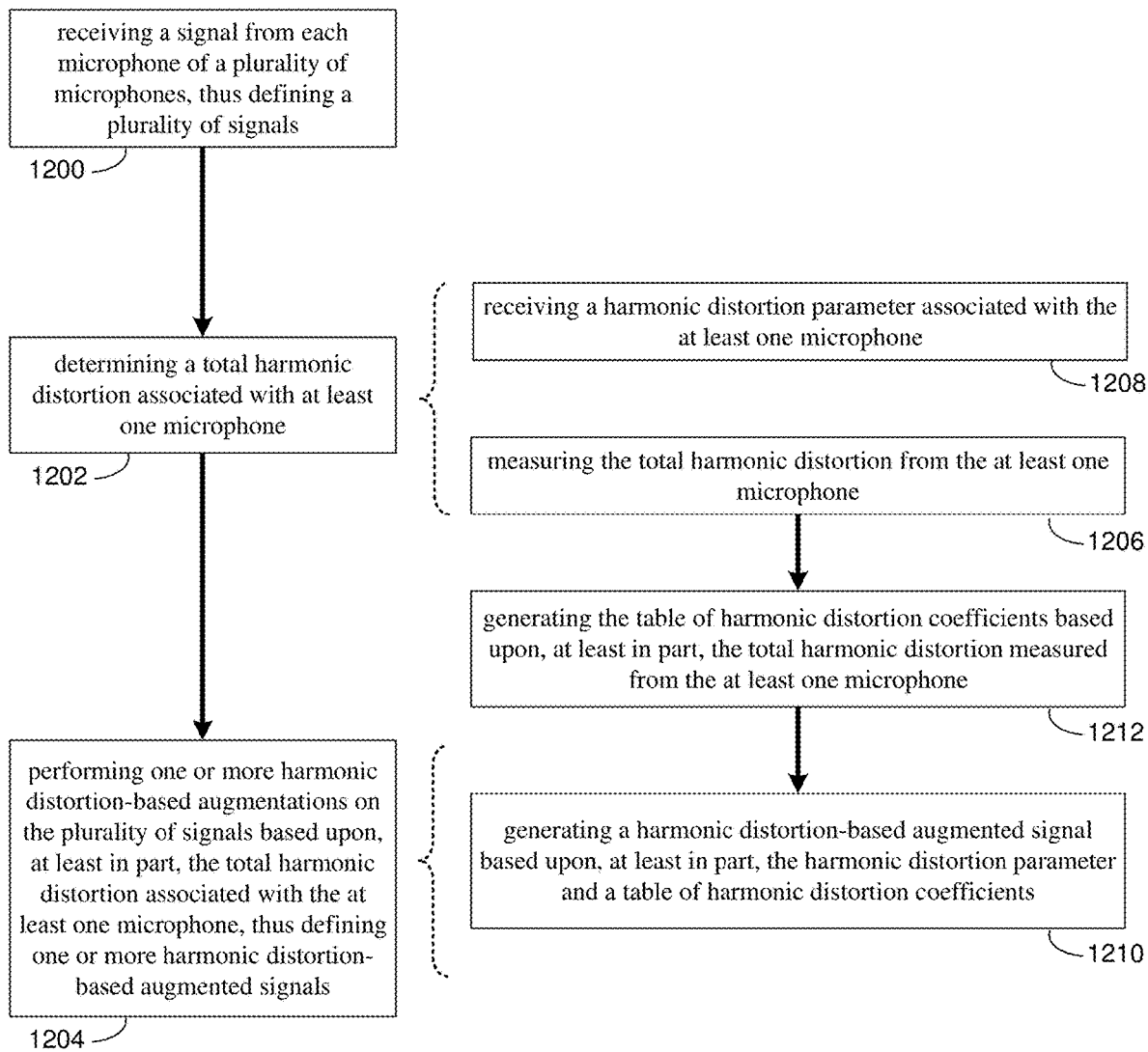
FIG. 12 is a flow chart of one implementation of the data augmentation process of FIG. 1.

As discussed above and referring also at least to FIGS. 12-13, data augmentation process 10 may receive 1200 a signal from each microphone of a plurality of microphones, thus defining a plurality of signals. Harmonic distortion associated with at least one microphone may be determined 1202. One or more harmonic distortion-based augmentations may be performed 1204 on the plurality of signals based upon, at least in part, the harmonic distortion associated with the at least one microphone, thus defining one or more harmonic distortion-based augmented signals.

Figure 13:
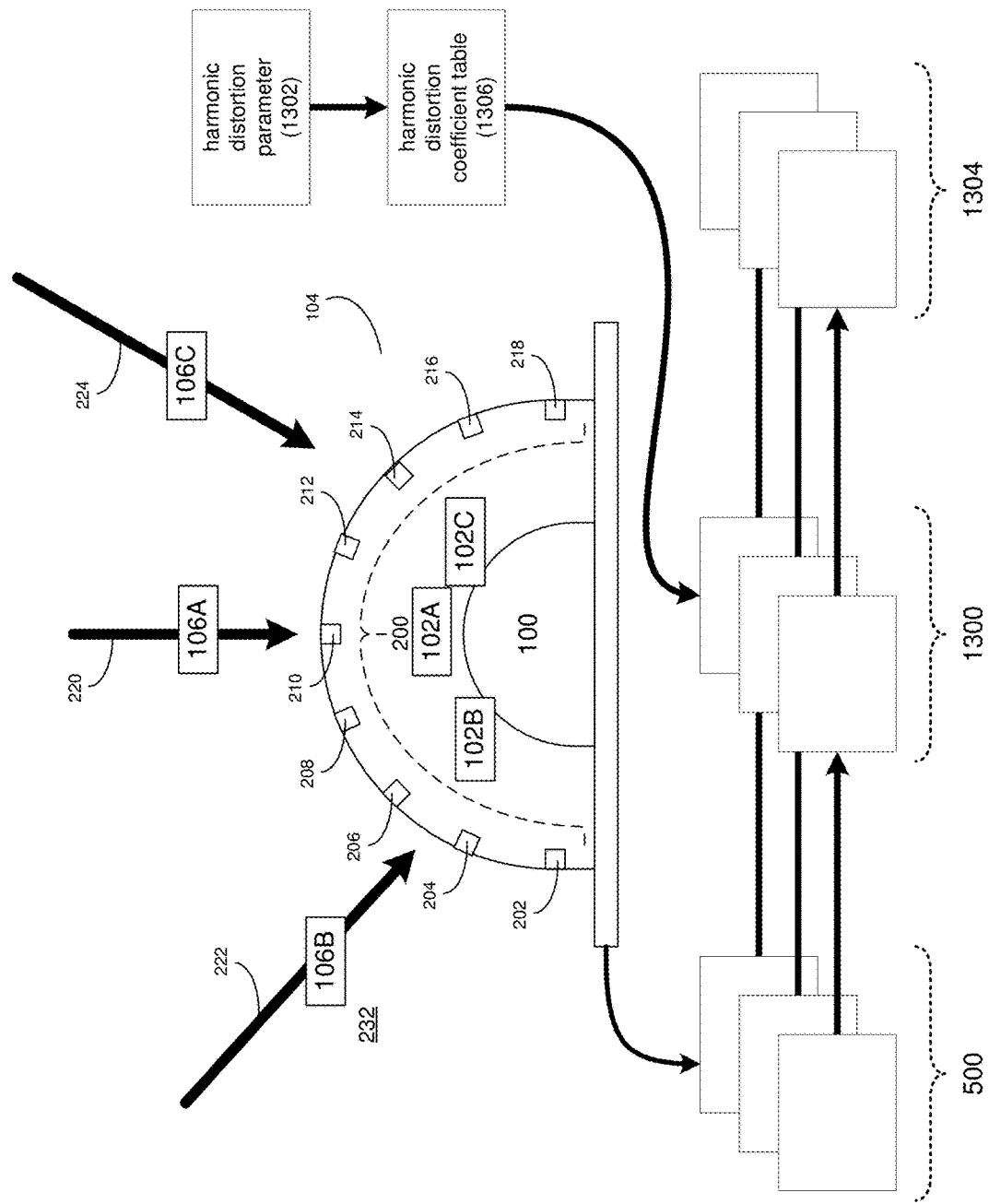
FIG. 13 is a diagrammatic view of a modular ACD system according to one implementation of the data augmentation process of FIG. 1.

Referring also to FIG. 13 and in some implementations, audio recording system 104 may include directional microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. In some implementations, each audio acquisition device or microphone may include a microphone assembly, an amplifier, and an analog-to-digital system. As discussed above, each microphone (e.g., audio acquisition devices 202, 204, 206, 208, 210, 212, 214, 216, 218) may have imperfections and/or mismatch in the configuration or operation of each microphone.

For example, each microphone of microphone array 200 may include various physical characteristics that impact the ability of each microphone to process speech signals. In some implementations, the combination of the microphone assembly, the amplifier, and/or the analog-to-digital system may introduce harmonic distortions. In some implementations, harmonic distortion may refer to a measure of the amount of distortion on the output of a microphone for a given pure tone input signal. In some implementations, varying total harmonic distortion values associated with one or more microphones of a microphone array may result in erroneous processing of speech signals by speech processing systems.

For example, suppose that microphone 208 outputs a first total harmonic distortion while microphone 218 outputs a second total harmonic distortion. In this example, the total harmonic distortion produced by each microphone may result in erroneous or inaccurate signal processing by a speech processing system (e.g., speech processing system 300). Accordingly, data augmentation process 10 may perform 1204 augmentations to existing training data and/or signals received 1200 from various microphones to generate harmonic distortion-based augmented signals. These harmonic distortion-based augmented signals may be used to train speech processing system 300 to account for harmonic distortion generated by particular microphones of microphone array 200.

In some implementations, data augmentation process 10 may receive 1200 a signal from each microphone of a plurality of microphones, thus defining a plurality of signals. Referring again to FIG. 13 and in some implementations, microphone array 200 may process speech (e.g., audio encounter information 106A-106C) from various sources. Accordingly, microphones 202, 204, 206, 208, 210, 212, 214, 216, 218 may generate signals (e.g., plurality of signals 500) representative of the speech processed by microphone array 200. In some implementations, data augmentation process 10 may receive 1200 a signal from some or each of microphones 202, 204, 206, 208, 210, 212, 214, 216, 218.

In some implementations, data augmentation process 10 may determine 1202 a total harmonic distortion associated with at least one microphone. For example and as discussed above, the total harmonic distortion may refer to a measure of the amount of distortion on the output of a microphone for a given pure tone input signal. The output of the microphone may include a fundamental signal and a number of harmonics that are added together. In some implementations, data augmentation process 10 may receive a total harmonic distortion associated with at least one microphone (e.g., total harmonic distortions 1300). In some implementations, data augmentation process 10 may determine 1202 the total harmonic distortion associated with the at least one microphone by measuring 1206 the total harmonic distortion from the at least one microphone.

For example, data augmentation process 10 may input a sinusoidal signal of frequency "w" through each microphone (e.g., combination of microphone assembly, amplifier, and/or analog-to-digital system). In this example, additional content may be added at multiples of n*ω (harmonics) of the original frequency (i.e., "ω"). Data augmentation process 10 may determine the total harmonic distortion for each microphone by measuring the additional signal content not present in the input signal from the output signal. In some implementations, data augmentation process 10 may determine a number of harmonic orders (e.g., multiples of input frequency) for each microphone. As will be discussed in greater detail below, the number of harmonic orders of the total harmonic distortion may be used as a parameter (e.g., a harmonic distortion parameter) to perform one or more harmonic distortion-based augmentations.

Referring again to FIG. 13 and in some implementations, suppose data augmentation process 10 provides a pure sinusoidal input to at least one microphone (e.g., microphones 208, 218). In this example, data augmentation process 10 may measure 1206 any additional content (i.e., content not included in the input signal) from the output of microphones 208, 218. Accordingly, data augmentation process 10 may determine 1202 that microphone 208 outputs a first total harmonic distortion while microphone 218 outputs a second total harmonic distortion based upon, at least in part, the additional content from the output of microphones 208, 218. While an example of determining e.g., two total harmonic distortions associated with two microphones has been described, it will be appreciated that any number of total harmonic distortions for any number of microphones may be determined 1202 within the scope of the present disclosure.

In some implementations, determining 1202 the total harmonic distortion associated with the at least one microphone may include simulating one or more models representative of the total harmonic distortion. For example, the total harmonic distortion may be simulated using one or more machine learning models configured to "learn" the total harmonic distortion of individual microphones. As discussed above and as known in the art, a machine learning model may generally include an algorithm or combination of algorithms that has been trained to recognize certain types of patterns. In some implementations, a machine learning model (e.g., machine learning model 302) may be configured to simulate the operation of a microphone to generate the total harmonic distortion associated with at least one microphone (e.g., total harmonic distortions 1300).

In some implementations, determining 1202 the total harmonic distortion associated with the at least one microphone may include receiving 1208 a harmonic distortion parameter associated with the at least one microphone. Referring again to FIG. 13 and in some implementations, the harmonic distortion parameter (e.g., harmonic distortion parameter 1302) may indicate the order of harmonics associated with the at least one microphone. For example, harmonic distortion parameter 1302 may be a number of harmonics associated with or generated at the output of a microphone (e.g., a harmonic distortion parameter of "1" may reference a first order harmonic; a harmonic distortion parameter of "2" may reference a first and as second order harmonic; and a harmonic distortion parameter of "n" may reference "n" order harmonics). In some implementations, data augmentation process 10 may utilize a graphical user interface for receiving a selection of harmonic distortion parameter 1302. In some implementations, harmonic distortion parameter 1302 may be a default value that may be updated or replaced by a user-defined or selected value.

In some implementations, data augmentation process 10 may receive 1208 the harmonic distortion parameter associated with the at least one microphone in response to determining 1202 the total harmonic distortion associated with the at least one microphone. For example and as discussed above, when measuring or simulating the total harmonic distortions, data augmentation process 10 may determine the number of harmonics output by the at least one microphone. Continuing with the above example, suppose that data augmentation process 10 determines 1202 that microphone 208 outputs a total harmonic distortion with e.g., five harmonics. In this manner, data augmentation process 10 may define harmonic distortion parameter 1302 as e.g., five to represent the order of harmonics associated with microphone 208.

In some implementations, data augmentation process 10 may perform 1204 one or more harmonic distortion-based augmentations on the plurality of signals based upon, at least in part, the total harmonic distortion associated with the at least one microphone, thus defining one or more harmonic distortion-based augmented signals. A harmonic distortion-based augmented signal (e.g., harmonic distortion-based augmented signal 1304) may generally include an augmentation of a signal or training data to include augmentations in the signal representative of the addition of harmonic components output by a microphone. As discussed above, the harmonic distortion-based augmented signal may allow a speech processing system (e.g., speech processing system 300) to account for harmonic components generated in the output signals of a microphone without requiring the expensive and complex signal compensation techniques used in conventional speech processing systems with microphone arrays.

In some implementations, the one or more total harmonic distortions (e.g., total harmonic distortions 1300) may be associated with particular microphones or a microphone array. For example, suppose a speaker is speaking in a clinical environment with a microphone array of modular ACD system 54 deployed within the clinical environment. In this example, the properties of the microphones of the microphone array may output various total harmonic distortions. Now suppose the speaker addresses a virtual assistant within a separate computing device positioned within the clinical environment. In this example, while the environmental features remain the same (i.e., the clinical environment), the microphone array of the virtual assistant may have factors and characteristics that may impact the signal processing differently than the microphone array of modular ACD system 54. In some implementations, the distinctions between microphone arrays may have various impacts on the performance of speech processing systems. Accordingly, data augmentation process 10 may allow speech signals received by one microphone array to be used in the training of speech processing systems with other microphone arrays and/or for adapting a speech processing system or model with new adaptation data.

In some implementations, data augmentation process 10 may receive a selection of a target microphone or microphone array. A target microphone or microphone array may include a type of microphone or microphone array. In some implementations, data augmentation process 10 may receive a selection of a target microphone or microphone array by providing particular a total harmonic distortion associated with the target microphone or microphone array. In some implementations, data augmentation process 10 may utilize a graphical user interface for receiving a selection of a target microphone array from a library of target microphone arrays. In one example, data augmentations process 10 may receive selections (e.g., via a graphical user interface) of various characteristics of the microphone array (e.g., a type of microphone array, an arrangement of microphones in a microphone array, etc.) to define a target microphone array. In some implementations, data augmentation process 10 may receive a range or distribution of characteristics for the target microphone array. While an example of a graphical user interface has been described, it will be appreciated that a target microphone array may be selected in various ways within the scope of the present disclosure (e.g., manually by a user, automatically by data augmentation process 10, a pre-defined target microphone array, etc.).

In some implementations, data augmentation process 10 may perform 1204 one or more harmonic distortion-based augmentations on the plurality of signals based upon, at least in part, the total harmonic distortion associated with the at least one microphone. As will be discussed in greater detail below, it may be desirable to augment a plurality of signals associated with a particular microphone array for various reasons. For example and in some implementations, data augmentation process 10 may perform one or more harmonic distortion-based augmentations on the plurality of signals to utilize the plurality of signals for training a speech processing system with a target microphone array. In this example, data augmentation process 10 may train a speech processing system with speech signals received by a different microphone array which may allow for speech processing systems to be effectively utilized with various microphone arrays using an augmented set of training signals.

In another example, data augmentation process 10 may perform 1204 one or more harmonic distortion-based augmentations on the plurality of signals to generate additional training data for speech processing systems with varying total harmonic distortions among the same or similar types of microphone arrays. In this manner, data augmentation process 10 may train speech processing systems to be more robust against variations in harmonic distortions by augmenting a set of training data with various harmonic distortions or harmonic distortion distributions. While two examples have been provided for utilizing harmonic distortion-based augmented signals, it will be appreciated that data augmentation process 10 may perform harmonic distortion-based augmentations on the plurality of signals for various other purposes within the scope of the present disclosure. For example and in some implementations, harmonic distortion-based augmentations may be used to adapt a speech processing system with new adaptation data (e.g., harmonic distortion-based augmentations 1304).

In some implementations, performing 1204 the one or more harmonic distortion-based augmentations on the plurality of signals based upon, at least in part, the harmonic distortion parameter may include generating 1210 a harmonic distortion-based augmented signal based upon, at least in part, the harmonic distortion parameter and a table of harmonic distortion coefficients. For example, data augmentation process 10 may utilize harmonic distortion parameter 1302 and a table of harmonic distortion coefficients to generate one or more harmonic distortion-based augmented signals (e.g., harmonic distortion-based augmented signal 1306). In some implementations, data augmentation process 10 may reference a table of common total harmonic distortion coefficients (e.g., harmonic distortion coefficient table 1306) from a sample of measured devices (e.g., total harmonic distortions measured from multiple microphones). In some implementations, data augmentation process 10 may generate 1210 a harmonic distortion-based augmented signal based upon, at least in part, the harmonic distortion parameter and the table of harmonic distortion coefficients as shown below in Equation 1, where "N" is the order of the highest harmonic distortion (e.g., based upon the harmonic distortion parameter) and "p[N]" represents the contribution of the Nth harmonic to the total harmonic distortion:

$$\text{Harmonic distortion signal} = p[0] \cdot x^{N-1} + p[1] \cdot x^{N-2} + \ldots + p[N-2] \cdot x + p[N-1] \quad (1)$$

In some implementations, data augmentation process 10 may generate 1212 the table of harmonic distortion coefficients based upon, at least in part, the total harmonic distortion measured from the at least one microphone. In one example, suppose data augmentation process 10 measures 1206 the total harmonic distortion associated with microphone 208. As discussed above, suppose data augmentation process 10 provides a pure sinusoidal input to microphone 208. In this example, suppose data augmentation process 10 measures 1206 for any additional content (i.e., content not included in the input signal) from the output of microphone 208 and determines that microphone 208 outputs a total harmonic distortion with e.g., five harmonic components (e.g., first through fifth order harmonics in the output signal of microphone 208). Data augmentation process 10 may generate 1212 harmonic distortion coefficient table 1306 with one or more harmonic distortion coefficients based upon, at least in part, the output signal of microphone 208. While the example above describes generating a harmonic distortion coefficient table with harmonic distortion coefficients from a single microphone's total harmonic distortion, it will be appreciated that data augmentation process 10 may generate 1212 harmonic distortion coefficient table 1306 with any number of harmonic distortion coefficients for any number of microphones within the scope of the present disclosure.

Continuing with the above example, suppose that data augmentation process 10 determines 1202 that microphone 208 outputs a first total harmonic distortion with e.g., five harmonics. In this example, data augmentation process 10 may define harmonic distortion parameter 1302 for microphone 208 as "5" indicative of five harmonic components or orders. In some implementations, data augmentation process 10 may look up or identify one or more harmonic distortion coefficients to apply to Equation 1 with a harmonic distortion parameter of "5" for microphone 208. Accordingly, data augmentation process 10 may generate one or more harmonic distortion-based augmented signals 1304 from the plurality of signals (e.g., plurality of signals 500) based upon, at least in part, harmonic distortion parameter 1302 and harmonic distortion coefficient table 1306. In this manner, data augmentation process 10 may augment plurality of signals 500 to be more robust against the harmonic distortions of microphone 208. While the above example includes generating one or more harmonic distortion-based augmented signals based upon, at least in part, a harmonic distortion parameter associated with one microphone, it will be appreciated that any number of harmonic distortion-based augmented signals may be generated for any number of harmonic distortion parameter and/or total harmonic distortions determined for any number of microphones within the scope of the present disclosure.

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, not at all, or in any combination with any other flowcharts depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
receiving a signal from each microphone of a plurality of microphones, thus defining a plurality of signals;
determining a total harmonic distortion associated with at least one microphone; and
performing one or more harmonic distortion-based augmentations on the plurality of signals based upon, at least in part, the total harmonic distortion associated with the at least one microphone, thus defining one or more harmonic distortion-based augmented signals.

2. The computer-implemented method of claim 1, wherein determining the total harmonic distortion associated with the at least one microphone includes receiving a harmonic distortion parameter associated with the at least one microphone.

3. The computer-implemented method of claim 2, wherein the harmonic distortion parameter indicates an order of harmonics associated with the at least one microphone.

4. The computer-implemented method of claim 2, wherein performing the one or more harmonic distortion-based augmentations on the plurality of signals based upon, at least in part, the harmonic distortion parameter includes generating a harmonic distortion-based augmented signal based upon, at least in part, the harmonic distortion parameter and a table of harmonic distortion coefficients.

5. The computer-implemented method of claim 4, wherein determining the total harmonic distortion associated with the at least one microphone includes measuring the total harmonic distortion from the at least one microphone.

6. The computer-implemented method of claim 5, further comprising:
generating the table of harmonic distortion coefficients based upon, at least in part, the total harmonic distortion measured from the at least one microphone.

7. The computer-implemented method of claim 1, wherein the plurality of microphones define a microphone array.

8. A computer program product residing on a non-transitory computer readable medium having a plurality of instructions stored thereon which, when executed by a processor, cause the processor to perform operations comprising:
receiving a signal from each microphone of a plurality of microphones, thus defining a plurality of signals;
determining a total harmonic distortion associated with at least one microphone; and
performing one or more harmonic distortion-based augmentations on the plurality of signals based upon, at least in part, the total harmonic distortion associated with the at least one microphone, thus defining one or more harmonic distortion-based augmented signals.

9. The computer program product of claim 8, wherein determining the total harmonic distortion associated with the at least one microphone includes receiving a harmonic distortion parameter associated with the at least one microphone.

10. The computer program product of claim 9, wherein the harmonic distortion parameter indicates an order of harmonics associated with the at least one microphone.

11. The computer program product of claim 9, wherein performing the one or more harmonic distortion-based augmentations on the plurality of signals based upon, at least in part, the harmonic distortion parameter includes generating a harmonic distortion-based augmented signal based upon, at least in part, the harmonic distortion parameter and a table of harmonic distortion coefficients.

12. The computer program product of claim 11, wherein determining the total harmonic distortion associated with the at least one microphone includes measuring the total harmonic distortion from the at least one microphone.

13. The computer program product of claim 12, wherein the operations further comprise:
generating the table of harmonic distortion coefficients based upon, at least in part, the total harmonic distortion measured from the at least one microphone.

14. The computer program product of claim 8, wherein the plurality of microphones define a microphone array.

15. A computing system comprising:
a memory; and
a processor configured to receive a signal from each microphone of a plurality of microphones, thus defining a plurality of signals, wherein the processor is further configured to determine a total harmonic distortion associated with at least one microphone, and wherein the processor is further configured to perform one or more harmonic distortion-based augmentations on the plurality of signals based upon, at least in part, the total harmonic distortion associated with the at least one microphone, thus defining one or more harmonic distortion-based augmented signals.

16. The computing system of claim 15, wherein determining the total harmonic distortion associated with the at least one microphone includes receiving a harmonic distortion parameter associated with the at least one microphone.

17. The computing system of claim 16, wherein the harmonic distortion parameter indicates an order of harmonics associated with the at least one microphone.

18. The computing system of claim 16, wherein performing the one or more harmonic distortion-based augmentations on the plurality of signals based upon, at least in part, the harmonic distortion parameter includes generating a harmonic distortion-based augmented signal based upon, at least in part, the harmonic distortion parameter and a table of harmonic distortion coefficients.

19. The computing system of claim 18, wherein determining the total harmonic distortion associated with the at least one microphone includes measuring the total harmonic distortion from the at least one microphone.

20. The computing system of claim 15, wherein the processor is further configured to:
generate the table of harmonic distortion coefficients based upon, at least in part, the plurality of harmonic distortions measured from the at least one microphone.

* * * * *